US012310700B2

United States Patent
Ma et al.

(10) Patent No.: US 12,310,700 B2
(45) Date of Patent: *May 27, 2025

(54) SYSTEM AND METHOD FOR DETECTING INFLAMMATION IN A FOOT

(71) Applicant: Siren Care, Inc., San Francisco, CA (US)

(72) Inventors: Ran Ma, San Francisco, CA (US); Jie Fu, Shanghai (CN); Henk Jan Scholten, The Hague (NL)

(73) Assignee: Siren Care, Inc., San Francisco, CA (US)

( * ) Notice: Subject to any disclaimer, the term of this patent is extended or adjusted under 35 U.S.C. 154(b) by 203 days.

This patent is subject to a terminal disclaimer.

(21) Appl. No.: 18/179,326

(22) Filed: Mar. 6, 2023

(65) Prior Publication Data
US 2024/0023814 A1   Jan. 25, 2024

Related U.S. Application Data

(60) Continuation of application No. 16/840,157, filed on Apr. 3, 2020, now abandoned, which is a division of
(Continued)

(51) Int. Cl.
*A61B 5/00* (2006.01)
*A43B 3/34* (2022.01)
(Continued)

(52) U.S. Cl.
CPC ............... *A61B 5/01* (2013.01); *A43B 3/34* (2022.01); *A61B 5/0008* (2013.01); *A61B 5/447* (2013.01);
(Continued)

(58) Field of Classification Search
CPC ......... A61B 5/01; A61B 5/0008; A61B 5/447; A61B 5/6807; A61B 5/7271; A61B 5/746;
(Continued)

(56) References Cited

U.S. PATENT DOCUMENTS

D281,081 S   10/1985   Zwissler et al.
4,670,977 A   6/1987   Scrantom et al.
(Continued)

FOREIGN PATENT DOCUMENTS

CN   1226855 A   8/1999
CN   1924131 A   3/2007
(Continued)

OTHER PUBLICATIONS

Buckley, P. (2016). Smart socks help prevent diabetes complications, smart2zero.com, located at Ihttps://www.smart2zero.com/news/smart-socks-help-prevent-diabetes-complications, 1 total page.
(Continued)

*Primary Examiner* — May A Abouelela
(74) *Attorney, Agent, or Firm* — COOLEY LLP

(57) ABSTRACT

One variation of a method for detecting inflammation in a foot includes: accessing a first temperature measured through a left temperature sensor and a second temperature measured through a right temperature sensor at approximately a first time, the left temperature sensor arranged in a left sock and the right temperature sensor arranged in a right sock worn on the user's feet; calculating a baseline difference between the first and second temperatures based on confirmation of absence of inflammation in the user's left
(Continued)

and right feet at the first time; accessing a third temperature measured through the left temperature sensor and a fourth temperature measured through the right temperature sensor at approximately a second time; and in response to a second temperature difference—between the third and fourth temperatures—differing from the baseline difference by more than a threshold difference, issuing an alarm through the user interface.

20 Claims, 8 Drawing Sheets

Related U.S. Application Data application No. 16/221,340, filed on Dec. 14, 2018, now Pat. No. 10,638,937, which is a continuation of application No. 15/382,248, filed on Dec. 16, 2016, now Pat. No. 10,602,932.

(60) Provisional application No. 62/400,440, filed on Sep. 27, 2016, provisional application No. 62/268,295, filed on Dec. 16, 2015.

(51) Int. Cl.
*A61B 5/01* (2006.01)
*G01K 3/10* (2006.01)
*G01K 3/14* (2006.01)
*G01K 13/20* (2021.01)
*G16H 40/63* (2018.01)
*G16H 50/20* (2018.01)
*G16H 50/30* (2018.01)
*A61B 5/11* (2006.01)

(52) U.S. Cl.
CPC .......... *A61B 5/6807* (2013.01); *A61B 5/7271* (2013.01); *A61B 5/746* (2013.01); *G01K 3/10* (2013.01); *G01K 3/14* (2013.01); *G01K 13/20* (2021.01); *G16H 40/63* (2018.01); *G16H 50/20* (2018.01); *G16H 50/30* (2018.01); *A61B 5/002* (2013.01); *A61B 5/1118* (2013.01); *A61B 5/7275* (2013.01); *A61B 5/742* (2013.01); *A61B 5/743* (2013.01); *A61B 2505/07* (2013.01); *A61B 2562/046* (2013.01)

(58) Field of Classification Search
CPC ..... A61B 5/002; A61B 5/1118; A61B 5/7275; A61B 5/742; A61B 5/743; A61B 2505/07; A61B 2562/046; A43B 3/34; G01K 3/10; G01K 3/14; G01K 13/20; G16H 40/63; G16H 50/20; G16H 50/30
See application file for complete search history.

(56) References Cited

U.S. PATENT DOCUMENTS

| | | | |
|---|---|---|---|
| D316,119 S | 4/1991 | McDermott et al. | |
| 5,191,895 A * | 3/1993 | Koltringer | A61B 5/4824 600/549 |
| 5,216,202 A | 6/1993 | Yoshida et al. | |
| 5,361,133 A | 11/1994 | Brown et al. | |
| 5,446,452 A * | 8/1995 | Litton | F16C 19/525 374/E1.004 |
| 5,546,955 A * | 8/1996 | Wilk | A61B 5/6807 600/592 |
| 5,642,096 A * | 6/1997 | Leyerer | A61B 5/1036 73/172 |
| 5,678,566 A * | 10/1997 | Dribbon | A61B 5/6829 600/592 |
| 5,729,966 A | 3/1998 | Grulick | |
| 5,788,114 A | 8/1998 | Perego | |
| 5,791,134 A | 8/1998 | Schneider et al. | |
| 5,929,332 A * | 7/1999 | Brown | A61B 5/1036 600/592 |
| 6,195,921 B1 * | 3/2001 | Truong | A43B 3/00 36/137 |
| 6,289,107 B1 | 9/2001 | Borchers et al. | |
| 6,329,917 B1 | 12/2001 | Leonard | |
| 6,398,740 B1 * | 6/2002 | Lavery | A61B 5/015 600/592 |
| 6,767,330 B2 | 7/2004 | Lavery et al. | |
| 7,395,614 B1 | 7/2008 | Bailey, Sr. et al. | |
| D589,524 S | 3/2009 | Orellana et al. | |
| 7,592,276 B2 | 9/2009 | Hill et al. | |
| 7,716,005 B2 | 5/2010 | Shoureshi et al. | |
| 8,360,987 B2 * | 1/2013 | Kantro | A61B 5/015 600/592 |
| D689,505 S | 9/2013 | Convay et al. | |
| 8,536,075 B2 | 9/2013 | Leonard | |
| D691,166 S | 10/2013 | Convay et al. | |
| 8,814,054 B2 | 8/2014 | Brun et al. | |
| 8,925,392 B2 | 1/2015 | Esposito et al. | |
| D732,055 S | 6/2015 | Schwartz | |
| 9,186,092 B2 * | 11/2015 | Mestrovic | A61B 5/1121 |
| 9,326,723 B2 * | 5/2016 | Petersen | A61B 5/6807 |
| 9,743,861 B2 | 8/2017 | Giedwoyn et al. | |
| 9,756,895 B2 | 9/2017 | Rice et al. | |
| 10,004,428 B2 | 6/2018 | Everett et al. | |
| D822,053 S | 7/2018 | Linders et al. | |
| 10,026,292 B2 | 7/2018 | Baker et al. | |
| 10,159,440 B2 * | 12/2018 | Longinotti-Buitoni | A61B 5/02055 |
| D837,237 S | 1/2019 | Fraser et al. | |
| 10,206,589 B2 | 2/2019 | Walker | |
| 10,292,652 B2 | 5/2019 | Berg et al. | |
| 10,295,169 B2 | 5/2019 | Athauda et al. | |
| 10,301,751 B2 | 5/2019 | Dias et al. | |
| 10,306,687 B2 | 5/2019 | Folske et al. | |
| 10,321,832 B2 | 6/2019 | Berg et al. | |
| 10,325,472 B1 | 6/2019 | Harsdorff et al. | |
| 10,327,700 B2 | 6/2019 | Lee et al. | |
| 10,383,550 B2 | 8/2019 | Hyde et al. | |
| 10,398,376 B2 | 9/2019 | Berg et al. | |
| 10,480,104 B2 | 11/2019 | Fu et al. | |
| 10,557,220 B2 | 2/2020 | Fu et al. | |
| 10,602,932 B2 | 3/2020 | Ma et al. | |
| 10,638,937 B2 | 5/2020 | Ma et al. | |
| 10,687,562 B2 | 6/2020 | Donohoe et al. | |
| D916,834 S | 4/2021 | Cone et al. | |
| 11,103,699 B1 | 8/2021 | Oppenheim et al. | |
| 11,109,807 B2 | 9/2021 | Fu et al. | |
| 11,147,510 B2 | 10/2021 | McMillen et al. | |
| D950,400 S | 5/2022 | Fu et al. | |
| 11,447,896 B2 | 9/2022 | Fu et al. | |
| 11,627,883 B2 | 4/2023 | Linders et al. | |
| 11,891,730 B2 | 2/2024 | Fu et al. | |
| 11,911,180 B2 | 2/2024 | Fu et al. | |
| 2002/0082486 A1 * | 6/2002 | Lavery | A61B 5/01 600/300 |
| 2002/0195442 A1 | 12/2002 | Lee | |
| 2003/0186228 A1 | 10/2003 | McDevitt et al. | |
| 2004/0009729 A1 | 1/2004 | Hill et al. | |
| 2005/0049816 A1 | 3/2005 | Oda et al. | |
| 2005/0070778 A1 | 3/2005 | Lackey et al. | |
| 2005/0171456 A1 | 8/2005 | Hirschman et al. | |
| 2006/0084848 A1 | 4/2006 | Mitchnick | |
| 2007/0000154 A1 | 1/2007 | DiBenedetto et al. | |
| 2007/0006489 A1 | 1/2007 | Case, Jr. et al. | |
| 2007/0194130 A1 | 8/2007 | Bauer | |
| 2007/0246334 A1 | 10/2007 | Elkins | |
| 2008/0109183 A1 * | 5/2008 | Shoureshi | G01K 1/026 374/E13.002 |
| 2008/0214962 A1 * | 9/2008 | Kantro | A61B 5/6829 600/592 |
| 2009/0053950 A1 | 2/2009 | Surve | |
| 2009/0076772 A1 | 3/2009 | Hinshaw et al. | |
| 2009/0139198 A1 | 6/2009 | Dias et al. | |
| 2010/0185398 A1 | 7/2010 | Berns et al. | |

(56) References Cited

U.S. PATENT DOCUMENTS

| | | | |
|---|---|---|---|
| 2010/0261530 A1 | 10/2010 | Thomas et al. | |
| 2010/0324455 A1 | 12/2010 | Rangel et al. | |
| 2011/0010924 A1 | 1/2011 | Berger et al. | |
| 2011/0015498 A1* | 1/2011 | Mestrovic | A61B 5/01 600/592 |
| 2011/0054359 A1 | 3/2011 | Sazonov et al. | |
| 2011/0214501 A1* | 9/2011 | Ross | A43B 7/00 73/172 |
| 2012/0109013 A1* | 5/2012 | Everett | A61B 5/1036 600/587 |
| 2013/0002533 A1 | 1/2013 | Burroughs et al. | |
| 2013/0053677 A1 | 2/2013 | Schoenfeld | |
| 2013/0072765 A1 | 3/2013 | Kahn et al. | |
| 2013/0092742 A1 | 4/2013 | Brun et al. | |
| 2013/0137943 A1* | 5/2013 | Pinto Rodrigues | A61B 5/4866 600/595 |
| 2013/0145588 A1 | 6/2013 | Nakata | |
| 2013/0166079 A1 | 6/2013 | Wilhelm et al. | |
| 2013/0185003 A1 | 7/2013 | Carbeck et al. | |
| 2013/0192071 A1* | 8/2013 | Esposito | A43B 17/00 324/693 |
| 2013/0211281 A1 | 8/2013 | Ross et al. | |
| 2013/0213145 A1 | 8/2013 | Owings et al. | |
| 2013/0213147 A1 | 8/2013 | Rice et al. | |
| 2013/0258085 A1 | 10/2013 | Leedy et al. | |
| 2013/0261494 A1* | 10/2013 | Bloom | A61B 5/0075 600/549 |
| 2014/0121479 A1* | 5/2014 | O'Connor | A61B 5/447 600/407 |
| 2014/0121532 A1* | 5/2014 | O'Connor | A61B 5/1074 600/476 |
| 2014/0142396 A1* | 5/2014 | Ricks | G16H 40/67 600/301 |
| 2014/0222173 A1 | 8/2014 | Giedwoyn et al. | |
| 2014/0268099 A1 | 9/2014 | Moslehi | |
| 2014/0276235 A1 | 9/2014 | Raniere | |
| 2014/0288669 A1 | 9/2014 | Sanders et al. | |
| 2014/0378786 A1 | 12/2014 | Hong et al. | |
| 2015/0025332 A1 | 1/2015 | Yang | |
| 2015/0057562 A1* | 2/2015 | Linders | A61B 5/015 600/549 |
| 2015/0091820 A1 | 4/2015 | Rosenberg et al. | |
| 2015/0094544 A1 | 4/2015 | Spolin et al. | |
| 2015/0105687 A1 | 4/2015 | Abreu | |
| 2015/0157263 A1 | 6/2015 | Workman et al. | |
| 2015/0173666 A1 | 6/2015 | Smith et al. | |
| 2015/0173679 A1* | 6/2015 | West | A61B 5/6803 600/549 |
| 2015/0177080 A1 | 6/2015 | Esposito et al. | |
| 2015/0190059 A1* | 7/2015 | Petersen | A61B 5/0022 600/549 |
| 2015/0201846 A1 | 7/2015 | Maiershon et al. | |
| 2015/0297100 A1 | 10/2015 | Castillo | |
| 2015/0351493 A1 | 12/2015 | Ashcroft et al. | |
| 2015/0359457 A1 | 12/2015 | Blumenthal et al. | |
| 2016/0011091 A1 | 1/2016 | Huang et al. | |
| 2016/0038037 A1 | 2/2016 | Kovacs | |
| 2016/0066818 A1 | 3/2016 | Cowley et al. | |
| 2016/0066821 A1* | 3/2016 | Mestrovic | A61B 5/1121 600/592 |
| 2016/0100720 A1 | 4/2016 | Holguin | |
| 2016/0135743 A1 | 5/2016 | Cobbett et al. | |
| 2016/0180447 A1 | 6/2016 | Kamalie et al. | |
| 2016/0192716 A1 | 7/2016 | Lee | |
| 2016/0192856 A1 | 7/2016 | Lee | |
| 2016/0192862 A1 | 7/2016 | Merrell et al. | |
| 2016/0206242 A1 | 7/2016 | Esposito et al. | |
| 2016/0249174 A1 | 8/2016 | Patel et al. | |
| 2016/0256706 A1 | 9/2016 | Harrison | |
| 2016/0299526 A1 | 10/2016 | Inagaki et al. | |
| 2016/0310032 A1 | 10/2016 | Sotzing et al. | |
| 2016/0338621 A1 | 11/2016 | Kanchan et al. | |
| 2016/0367191 A1 | 12/2016 | Esposito et al. | |
| 2017/0127734 A1 | 5/2017 | Roberts et al. | |
| 2017/0188841 A1 | 7/2017 | Ma et al. | |
| 2017/0188950 A1 | 7/2017 | Gazdag et al. | |
| 2017/0231551 A1 | 8/2017 | Fleischer et al. | |
| 2017/0273569 A1 | 9/2017 | Barber et al. | |
| 2017/0275789 A1 | 9/2017 | Dias et al. | |
| 2017/0333256 A1 | 11/2017 | Bassez et al. | |
| 2017/0339524 A1 | 11/2017 | Cho et al. | |
| 2017/0345279 A1 | 11/2017 | Abraham et al. | |
| 2018/0000367 A1 | 1/2018 | Longinotti-Buitoni | |
| 2018/0003579 A1 | 1/2018 | Esposito et al. | |
| 2018/0042513 A1 | 2/2018 | Connor | |
| 2018/0220962 A1 | 8/2018 | Palley et al. | |
| 2018/0263510 A1 | 9/2018 | Cronin et al. | |
| 2018/0295895 A1 | 10/2018 | Donohoe et al. | |
| 2018/0295897 A1 | 10/2018 | Donohoe et al. | |
| 2018/0307314 A1 | 10/2018 | Connor | |
| 2018/0317597 A1 | 11/2018 | Maxey et al. | |
| 2018/0317820 A1 | 11/2018 | Pace et al. | |
| 2019/0094088 A1 | 3/2019 | Reif et al. | |
| 2019/0283394 A1 | 9/2019 | Ashcroft et al. | |
| 2019/0287374 A1 | 9/2019 | Harsdorff et al. | |
| 2019/0298265 A1 | 10/2019 | Keating et al. | |
| 2019/0313913 A1 | 10/2019 | Fu et al. | |
| 2019/0320939 A1 | 10/2019 | Orvis et al. | |
| 2019/0335843 A1 | 11/2019 | Lu et al. | |
| 2020/0000180 A1 | 1/2020 | Sherrah et al. | |
| 2020/0222001 A1 | 7/2020 | Fu et al. | |
| 2020/0245724 A1 | 8/2020 | Kobe et al. | |
| 2020/0253482 A1 | 8/2020 | Ma et al. | |
| 2020/0289028 A1 | 9/2020 | Oumnia | |
| 2020/0353239 A1 | 11/2020 | Daniels et al. | |
| 2020/0375470 A1 | 12/2020 | Fu et al. | |
| 2021/0046356 A1 | 2/2021 | Czaja et al. | |
| 2021/0077304 A1 | 3/2021 | Xu et al. | |
| 2021/0145622 A1 | 5/2021 | Riffel et al. | |
| 2021/0298674 A1 | 9/2021 | Fu et al. | |
| 2022/0175317 A1 | 6/2022 | Fu et al. | |
| 2022/0389626 A1 | 12/2022 | Fu et al. | |
| 2023/0240542 A1 | 8/2023 | Linders et al. | |

FOREIGN PATENT DOCUMENTS

| | | |
|---|---|---|
| CN | 101411551 A | 4/2009 |
| CN | 203914881 U | 11/2014 |
| CN | 104219999 A | 12/2014 |
| CN | 104746194 A | 7/2015 |
| CN | 104766116 A | 7/2015 |
| CN | 105030248 A | 11/2015 |
| CN | 105188533 A | 12/2015 |
| CN | 106132291 A | 11/2016 |
| CN | 206620844 U | 11/2017 |
| CN | 107669247 A | 2/2018 |
| CN | 108471946 A | 8/2018 |
| CN | 108697341 A | 10/2018 |
| DE | 10 2011 012 458 A1 | 8/2012 |
| EP | 2 591 717 B1 | 8/2016 |
| GB | 2 426 255 A | 11/2006 |
| GB | 2 472 025 A | 1/2011 |
| GB | 2 472 026 A | 1/2011 |
| JP | 2008-138350 A | 6/2008 |
| WO | WO-02/095839 A2 | 11/2002 |
| WO | WO-02/095839 A3 | 11/2002 |
| WO | WO-2008/080245 A2 | 7/2008 |
| WO | WO-2008-080245 A3 | 7/2008 |
| WO | WO-2009/005373 A1 | 1/2009 |
| WO | WO-2011/010093 A1 | 1/2011 |
| WO | WO-2014/179343 A1 | 11/2014 |
| WO | WO-2015/143218 A1 | 9/2015 |
| WO | WO-2016/038342 A1 | 3/2016 |
| WO | WO-2017/048979 A1 | 3/2017 |
| WO | WO-2017/079628 A1 | 5/2017 |
| WO | WO-2017/106760 A1 | 6/2017 |
| WO | WO-2017/115083 A1 | 7/2017 |
| WO | WO-2017/120063 A1 | 7/2017 |
| WO | WO-2017/172781 A1 | 10/2017 |

(56) References Cited

FOREIGN PATENT DOCUMENTS

WO     WO-2017/175001 A1     10/2017
WO     WO-2018/064174 A1     4/2018

OTHER PUBLICATIONS

Buhr, S. (2016). Siren Care makes a "smart" sock to track diabetic health, techcrunch.com (online), located at https://techcrunch.com/2016/11/25/siren-care-makes-a-smart-sock-to-track-diabetic-health/, 2 total pages.
Corrected Notice of Allowability mailed on Mar. 2, 2020, for U.S. Appl. No. 15/382,248, filed Dec. 16, 2016, 2 pages.
Corrected Notice of Allowability mailed on Apr. 8, 2020, for U.S. Appl. No. 16/221,340, filed Dec. 14, 2018, 3 pages.
Extended European Search Report mailed on Apr. 9, 2019, for EP Application No. 16 876 847.1, filed on Dec. 16, 2016, 11 pages.
Extended European Search Report mailed on Aug. 21, 2020, for EP Application No. 17 857 336.6, filed on Sep. 27, 2017, 9 pages.
Extended European Search Report mailed on Sep. 3, 2021, for EP Application No. 19 757 800., filed on Feb. 20, 2019, 11 pages.
Extended European Search Report mailed on Jun. 5, 2023, for EP Application No. 19 896 007.2, filed on Jun. 21, 2019, 11 pages.
Final Office Action mailed on Jul. 12, 2019, for U.S. Appl. No. 16/221,340, filed Dec. 14, 2018, 13 pages.
Final Office Action mailed on Oct. 19, 2020, for U.S. Appl. No. 16/836,800, filed Mar. 31, 2020, 14 pages.
Final Office Action mailed on Sep. 10, 2021, for U.S. Appl. No. 16/381,818, filed Apr. 11, 2019, 16 pages.
Hardy, D.A. et al. (2019). "Automated insertion of package dies onto wire and into a textile yarn sheath," Microsystem Technologies, pp. 1-13.
Hughes-Riley, T et al. (2017). "A Study of Thermistor Performance within a Textile Structure," Sensors 17:1804, 14 total pages.
International Search Report mailed on Mar. 27, 2017, for PCT Application No. PCT/US2016/067344, filed on Dec. 16, 2016, 3 pages.
International Search Report mailed on Feb. 6, 2018, for PCT Application No. PCT/US2017/053738, filed on Sep. 27, 2017, 4 pages.
International Search Report mailed on May 1, 2019, for PCT Application No. PCT/US2019/018714, filed on Feb. 20, 2019, 2 pages.
International Search Report mailed on Aug. 6, 2019, for PCT Application No. PCT/US2019/027050, filed on Apr. 11, 2019, 4 pages.
International Search Report mailed on Sep. 10, 2019, for PCT Application No. PCT/CN2018/0121244, filed on Dec. 14, 2018, 6 pages.
International Search Report mailed on Aug. 27, 2019, for PCT Application No. PCT/CN2019/092201, filed on Jun. 21, 2019, 5 pages.
International Search Report mailed on Aug. 28, 2019, for PCT Application No. PCT/CN2018/121246, filed on Dec. 14, 2018, 5 pages.
Introducing Siren's Diabetic Socks and Foot Monitoring System (2018). Youtube.com (online), accessed Jul. 19, 2021, available online at https://www.youtube.com/watch?v=IjMZu-PiSx4 (copy of video unavailable).
Medical and Health Care Icon Set (2017). iconfinder.com (online), accessed Aug. 3, 2021, available at https://www.iconfinder.com/iconsets/medical-health-care-flat.
Nashed, M-N. et al. (2019). "A novel method for embedding semiconductor dies within textile yarn to create electronic textiles," Fibers 7:12, 17 total pages.
Non-Final Office Action mailed on Mar. 4, 2019, for U.S. Appl. No. 16/221,340, filed Dec. 14, 2018, 17 pages.
Non-Final Office Action mailed on Jul. 8, 2019, for U.S. Appl. No. 15/382,248, filed Dec. 16, 2016, 21 pages.
Non-Final Office Action mailed on May 21, 2020, for U.S. Appl. No. 16/836,800, filed Mar. 31, 2020, 16 pages.
Non-Final Office Action mailed on Apr. 29, 2021, for U.S. Appl. No. 16/381,818, filed Apr. 11, 2019, 18 pages.
Non-Final Office Action mailed on Jul. 28, 2021, for U.S. Appl. No. 16/737,753, filed Jan. 8, 2020, 9 pages.
Non-Final Office Action mailed on Aug. 23, 2021, for U.S. Appl. No. 29/694,472, filed Jun. 11, 2019, 13 pages.
Non-Final Office Action mailed on Apr. 5, 2022, for U.S. Appl. No. 16/381,818, filed Apr. 11, 2019, 14 pages.
Non-Final Office Action mailed on Sep. 6, 2022, for U.S. Appl. No. 16/840,157, filed Apr. 30, 2020, 15 pages.
Non-Final Office Action mailed on Mar. 28, 2023, for U.S. Appl. No. 17/378,208, filed Jul. 16, 2021, 19 pages.
Notice of Allowance mailed on May 30, 2019, for U.S. Appl. No. 15/717,473, filed Sep. 27, 2017, 9 pages.
Notice of Allowance mailed on Oct. 31, 2019, for U.S. Appl. No. 15/717,473, filed Sep. 27, 2017, 5 pages.
Notice of Allowance mailed on Sep. 10, 2019, for U.S. Appl. No. 15/717,498, filed Sep. 27, 2017, 14 pages.
Notice of Allowance mailed on Jan. 2, 2020, for U.S. Appl. No. 15/382,248, filed Dec. 16, 2016, 17 pages.
Notice of Allowance mailed on Jan. 8, 2020, for U.S. Appl. No. 16/221,340, filed Dec. 14, 2018, 12 pages.
Notice of Allowance mailed on Oct. 15, 2020, for U.S. Appl. No. 29/694,472, filed Jun. 11, 2019, 14 pages.
Notice of Allowance mailed on May 18, 2021, for U.S. Appl. No. 16/836,800, filed Mar. 31, 2020, 9 pages.
Notice of Allowance mailed on Jan. 5, 2022, for U.S. Appl. No. 29/730,291, filed Apr. 2, 2020, 9 pages.
Notice of Allowance mailed on Jan. 14, 2022, for U.S. Appl. No. 29/730,291, filed Apr. 2, 2020, 3 pages.
Notice of Allowance mailed on Feb. 18, 2022, for U.S. Appl. No. 16/737,753, filed Jan. 8, 2020, 5 pages.
Notice of Allowance mailed on Sep. 21, 2023, for U.S. Appl. No. 17/887,374, filed Aug. 12, 2022, 9 pages.
Written Opinion of the International Searching Authority mailed on Mar. 27, 2017, for PCT Application No. PCT/US2016/067344, filed on Dec. 16, 2016, 8 pages.
Written Opinion of the International Searching Authority mailed on Feb. 6, 2018, for PCT Application No. PCT/US2017/053738, filed on Sep. 27, 2017, 10 pages.
Written Opinion of the International Searching Authority mailed on May 1, 2019, for PCT Application No. PCT/US2019/018714, filed on Feb. 20, 2019, 4 pages.
Written Opinion of the International Searching Authority mailed on Aug. 6, 2019, for PCT Application No. PCT/US2019/027050, filed on Apr. 11, 2019, 9 pages.
Written Opinion of the International Searching Authority mailed on Sep. 10, 2019, for PCT Application No. PCT/CN2018/0121244, filed on Dec. 14, 2018, 5 pages.
Written Opinion of the International Searching Authority mailed on Aug. 27, 2019, for PCT Application No. PCT/CN2019/092201, filed on Jun. 21, 2019, 4 pages.
Written Opinion of the International Searching Authority mailed on Aug. 28, 2019, for PCT Application No. PCT/CN2018/121246, filed on Dec. 14, 2018, 4 pages.
Corrected Notice of Allowability mailed on Nov. 3, 2023, for U.S. Appl. No. 17/378,208, filed Jul. 16, 2021, 3 pages.
International Search Report mailed on Sep. 1, 2022, for PCT Application No. PCT/US2022/031192, filed on May 26, 2022, 2 pages.
Non-Final Office Action mailed on May 1, 2024, for U.S. Appl. No. 17/346,176, filed on Jun. 11, 2021, 14 pages.
Notice of Allowance mailed on Oct. 20, 2023, for U.S. Appl. No. 17/378,208, filed Jul. 16, 2021, 12 pages.
Written Opinion of the International Searching Authority mailed on Sep. 1, 2022, for PCT Application No. PCT/US2022/031192, filed on May 26, 2022, 7 pages.

* cited by examiner

SYSTEM AND METHOD FOR DETECTING INFLAMMATION IN A FOOT

CROSS-REFERENCE TO RELATED APPLICATIONS

This application is a continuation of U.S. patent application Ser. No. 16/840,157, filed on Apr. 3, 2020, which is a divisional of U.S. patent application Ser. No. 16/221,340, filed on Dec. 14, 2018, now U.S. Pat. No. 10,638,937, which is a continuation of U.S. patent application Ser. No. 15/382,248, filed on Dec. 12, 2016, now U.S. Pat. No. 10,602,932, which claims the benefit of U.S. Provisional Application No. 62/268,295, filed on Dec. 16, 2015, and U.S. Provisional Application No. 62/400,440, filed on Sep. 27, 2016, each of which is hereby incorporated by reference in its entirety.

TECHNICAL FIELD

This invention relates generally to the field of foot care and more specifically to a new and useful system and method for detecting inflammation in a foot in the field of foot care.

DESCRIPTION OF THE EMBODIMENTS

The following description of embodiments of the invention is not intended to limit the invention to these embodiments but rather to enable a person skilled in the art to make and use this invention, Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
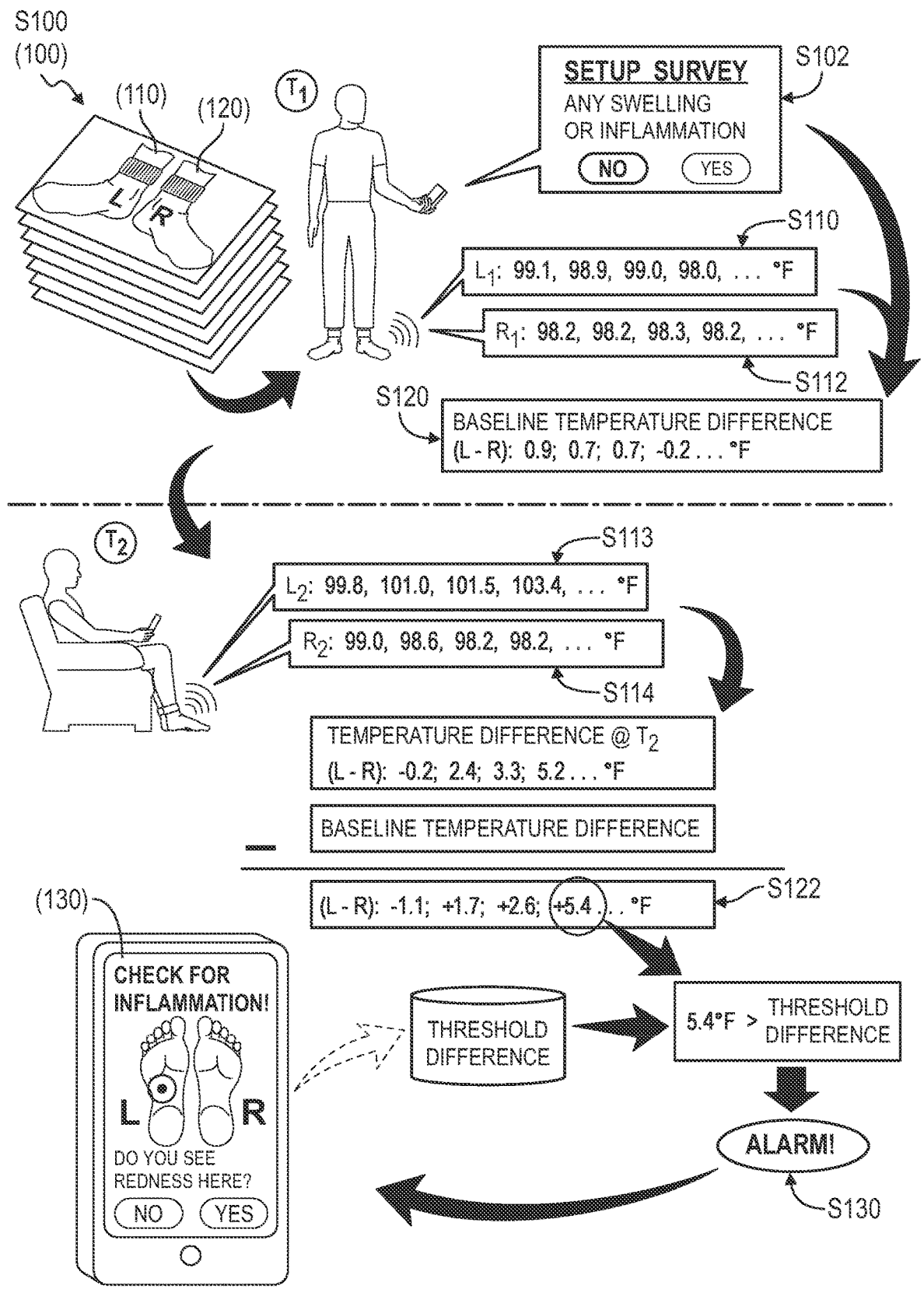
FIG. 1 is a flowchart representation of a method.

As shown in FIG. 1, a method S100 for detecting inflammation in a foot includes, in response to receipt of confirmation of absence of inflammation in a left foot of a user and a right foot of a user at a first time: accessing a first temperature measured through a left temperature sensor at approximately the first time in Block S110, the left temperature sensor arranged in a left sock worn on the left foot of the user; accessing a second temperature measured through a right temperature sensor at approximately the first time in Block S112, the right temperature sensor arranged in a right sock worn on the right foot of the user; and calculating a baseline temperature difference as a function of a difference between the first temperature and the second temperature in Block S120. The method S100 also includes: accessing a third temperature measured through the left temperature sensor at a second time succeeding the first time in Block S113; accessing a fourth temperature measured through the right temperature sensor at approximately the second time in Block S114; calculating a second temperature difference as a function of a difference between the third temperature and the fourth temperature in Block S122; and, in response to the second temperature difference differing from the baseline temperature difference by more than a threshold difference, issuing an alarm through the user interface in Block S130.

As shown in FIGS. 1-4, one variation of the method S100 includes: receiving confirmation of absence of inflammation in a left foot of a user and a right foot of a user through a user interface at a first time in Block S102; accessing a first temperature measured through a left temperature sensor at approximately the first time in Block S110, the left temperature sensor arranged in a left foot-borne device worn on the left foot of the user; accessing a second temperature measured through a right temperature sensor at approximately the first time in Block S112, the right temperature sensor arranged in a right foot-borne device worn on the right foot of the user; calculating a linear combination of the first temperature and the second temperature and storing the linear combination as a baseline temperature difference in response to confirmation of absence of inflammation in the left foot of the user and the right foot of the user in Block S120; accessing a third temperature measured through the left temperature sensor at a second time succeeding the first time in Block S113; accessing a fourth temperature measured through the right temperature sensor at approximately the second time in Block S114; calculating a second temperature difference as a function of a difference between the third temperature and the fourth temperature in Block S122; and in response to the second temperature difference differing from the baseline temperature difference by more than a threshold difference, issuing an alarm through the user interface in Block S130.

2. Applications

Generally, the method S100 can be executed by a computing device in cooperation with a set of socks (or other foot-borne devices) containing temperature sensors to collect temperatures across a user's feet and to interpret these temperatures as possible inflammation in one or both of the user's feet. In particular: a left sock worn on a user's left foot can regularly collect temperature values across the sole of the user's left foot through a left set of temperature sensors integrated into the left sock; a right sock worn on a user's right foot can regularly collect temperature values across the sole of the user's right foot through a right set of temperature sensors integrated into the right sock; and a computer program (hereinafter an "application") executing on the computer system can download these temperature values from the left and right socks, calculate temperature differences between like single temperature sensors or like groups of temperature sensors in the left and right socks, and then notify the user or an affiliated care provider of possible inflammation in one or both of the user's feet.

For example, a diabetic user may suffer from diabetic neuropathy and may therefore experience little or no feeling in her feet. Due to absence of feeling in her feet, the user may be limited in her ability to identify presence of a sore on her feet, an infection in her feet, or poor blood circulation through her feet; left untreated, such conditions may lead to greater medical complications for the user, including amputation of one or both feet. However, when a region of a foot becomes infected, the temperature of this region of the foot may rise as the body combats this infection.

Figure 2:
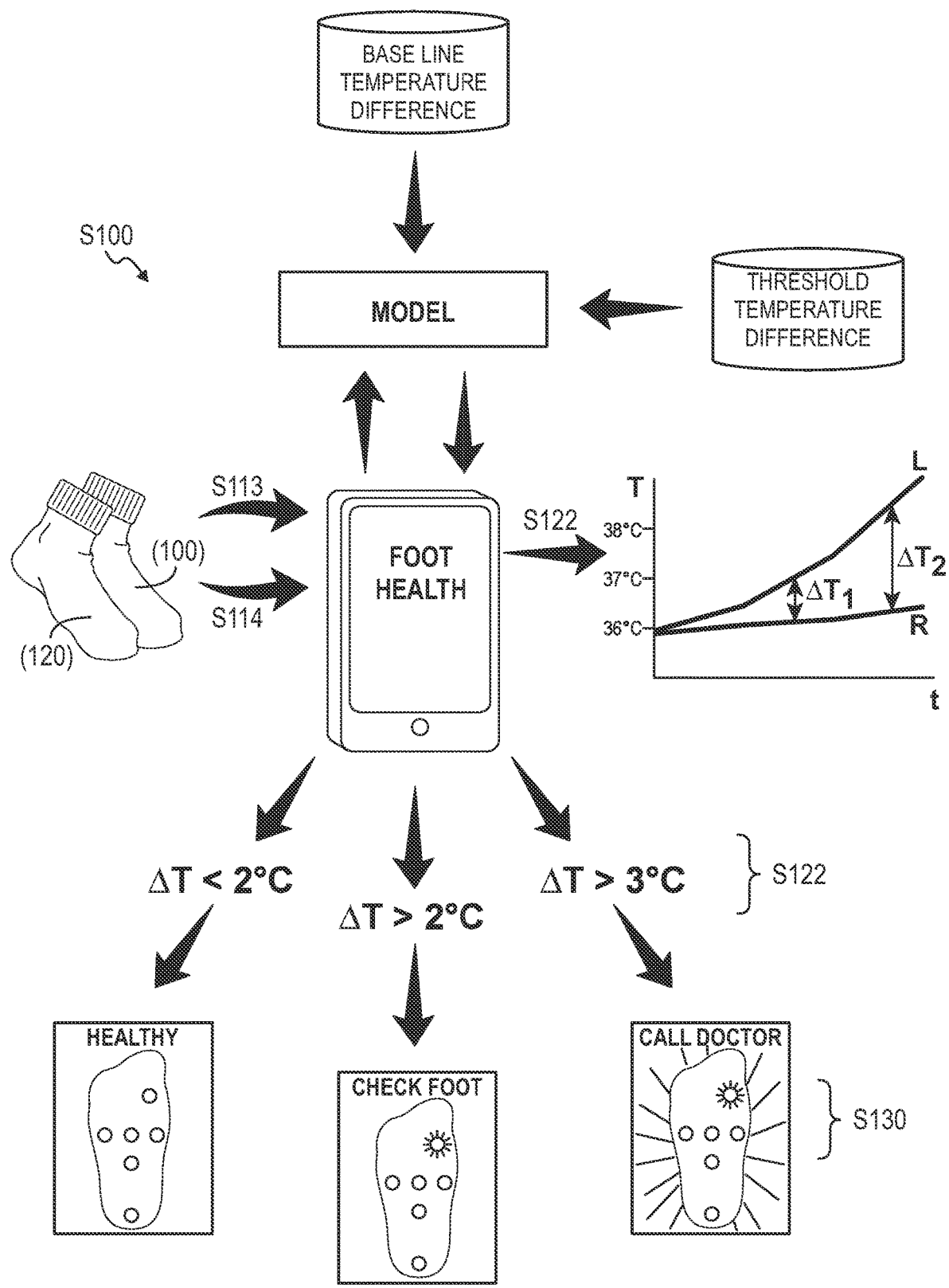
FIG. 2 is a flowchart representation of one variation of the method.

Therefore, the user may wear a left temperature-sensing-enabled sock, wear a right temperature-sensing-enabled sock, and connect these left and right socks with a computing device executing an application. The application can then execute Blocks of the method. S100 to monitor temperatures across the user's feet, to interpret these temperatures as possibly indicative of inflammation or other high-risk medical conditions in the user's feet, and to selectively prompt the user to visually inspect her feet, reduce her activity level, or see a care provider (e.g., a doctor) for treatment, as shown in FIG. 2. Therefore, the left sock, right sock, and application can cooperate to artificially detect the possible presence of a sore on the user's feet, to detect a possible infection in the user's feet, to detect poor blood circulation through the user's feet, and to communicate such conditions to the user when the user is unable to naturally detect such conditions due to diabetic neuropathy.

Figure 4:
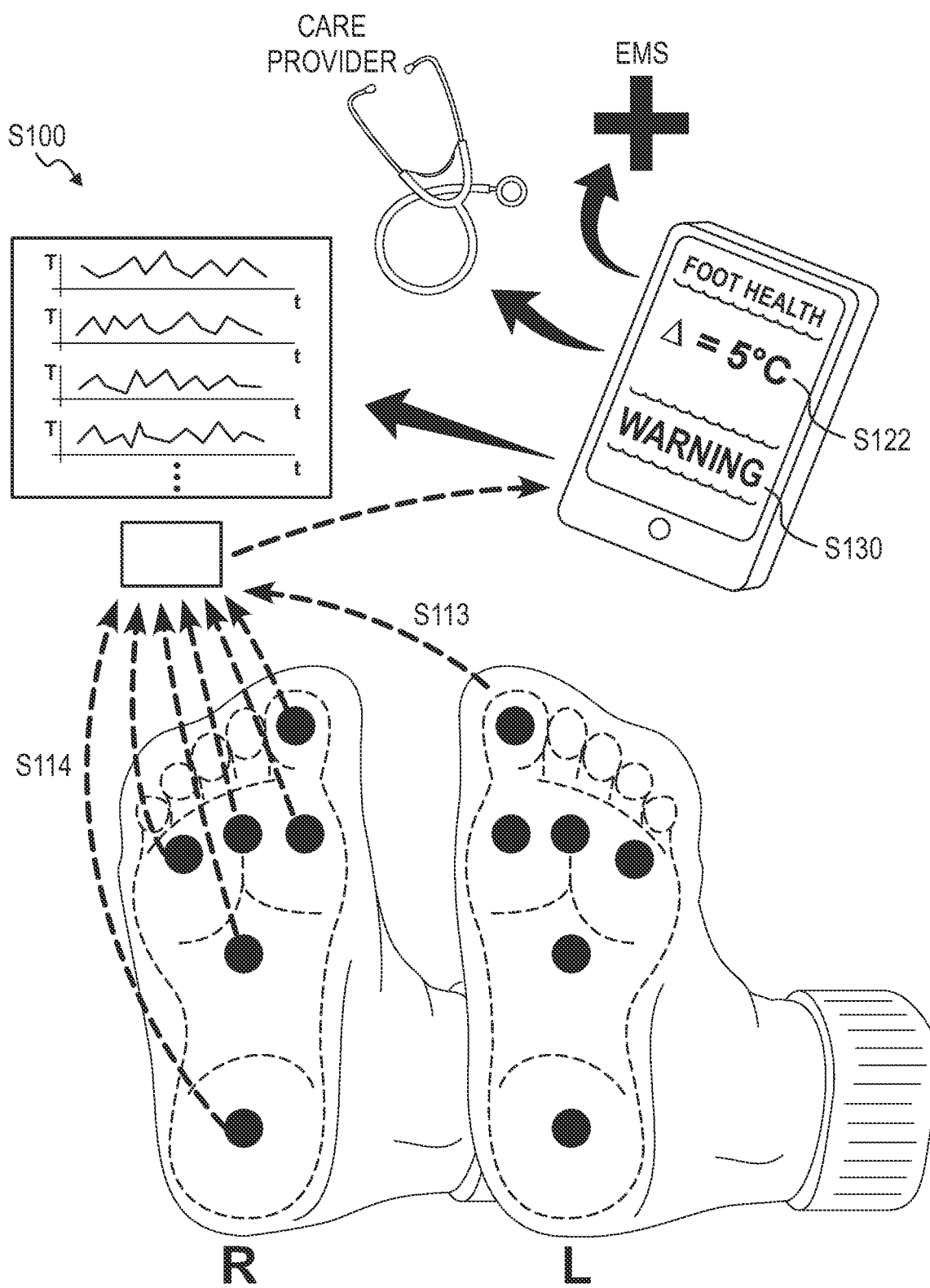
FIG. 4 is a flowchart representation of one variation of the method.
Figure 7:
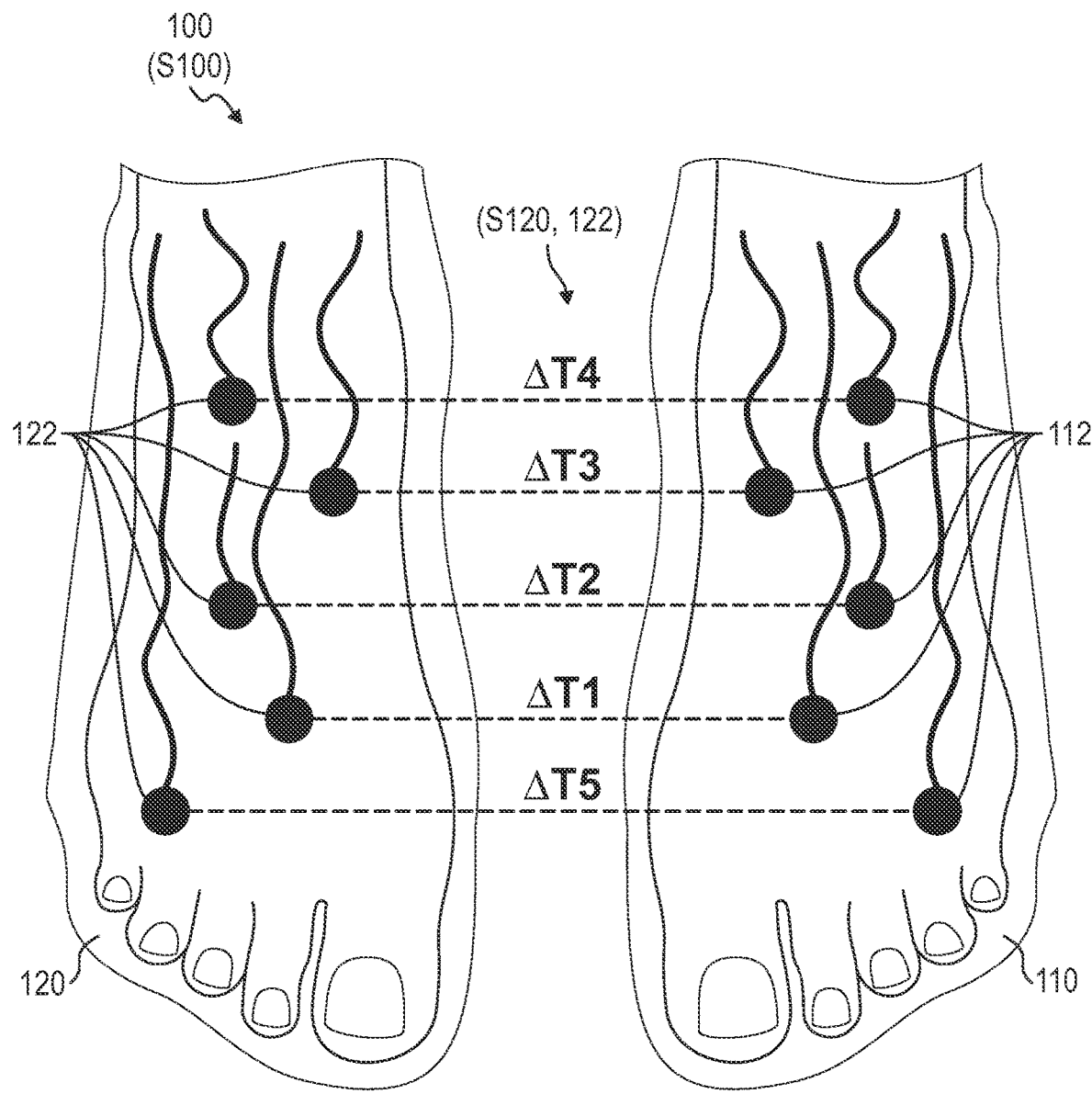
FIG. 7 is a schematic representation of one variation of the system.

In particular, the left sock can include a set of temperature sensors patterned across its sole; the right sock can include a similar set of temperature sensors arranged across its sole in a pattern that mirrors that of the temperature sensors in the left sock, as shown in FIGS. 4 and 7. When worn by a user, the left and right socks can: wirelessly connect to a local computing device executing the application; regularly sample these temperature sensors (e.g., at substantially similar times in five-minute intervals); and upload temperatures read from these temperature sensors to the computing device. For each sampling period, the application can then: calculate a difference between a singular temperature read from a first temperature sensor in the left sock and a singular temperature read from a first temperature sensor at the corresponding position in the right sock; and repeat this for each other temperature sensor pair in the left and right socks for the sampling period. (The application can similarly calculate differences between average temperatures of groups of temperature sensors across the left and right socks for one sampling period.) If one or more such temperature differences exceeds a preset threshold difference, the application can generate a notification prompting the user to inspect her feet or reduce her activity and render this notification on a display of the computing device.

However, inflammation and sores in a foot may increase relatively slowly over time (e.g., over hours or days), and a response to such inflammation within hours or even a day may be sufficient to limit complications. Therefore, the application can track differences between like temperature sensors or like groups of temperature sensors in the left and right socks over time and can issue an alarm if multiple temperature differences (e.g., a contiguous sequence of temperature differences calculated over a period of time or a threshold proportion of temperature differences calculated over a period of time) exceed the threshold difference, as shown in FIGS. 4 and 7. Similarly, the application can issue an alarm upon determining that temperature differences between like temperature sensors or like groups of temperature sensors in the left and right socks are increasing (or "trending upward") over time. In particular, by tracking changes in temperature differences between regions of the user's left and right feet over time, the application can identify a high rate of instances of possible inflammation (e.g., "true positives") and discard temporary changes in temperature difference that may be the result of external factors (e.g., "false positives," such as due to the user stepping on two surfaces of difference temperature or thermal conductivity) with limited additional risk to the user.

Furthermore, the user's left and right feet may naturally exhibit temperature differences generally or temperature differences at select regions, such as due to differences in circulation between the user's left and right feet. During a setup period, the application can therefore: receive confirmation from the user that inflammation is not present on either foot; retrieve temperature values from the left and right socks; calculate a temperature difference between a pair of like temperature sensors in the left and right socks; and store this temperature difference for this pair of like temperature sensors as a baseline temperature difference given such confirmation that no inflammation is present in the user's feet at this time, as shown in FIG. 1. (The application can additionally or alternatively define a baseline temperature difference between a linear combination (e.g., average) of temperatures read from like groups or clusters of temperature sensors in the left and right socks.) Outside of a setup period, the application can: calculate deviation of a temperature difference between two like temperature sensors groups of temperature sensors) in the left and right sock from the baseline temperature difference; and then issue an alarm if this temperature deviation exceeds the threshold difference. Over time, the application can also refine the baseline temperature difference based on additional temperatures read from the left and right socks and additional feedback—provided by the user, a doctor, or other care provider—confirming or refuting the presence of a sore, inflammation, or poor circulation in one or both of the user's feet. The application can therefore customize a baseline temperature difference for the user and implement and modify this baseline temperature difference over time in order to achieve a high true positive rate, low false positive rate, and low false negative rate for inflammation and/or other conditions in the user's feet.

The application can implement similar methods and techniques to customize a generic threshold difference for the user or to implement activity-specific threshold differences based on the user's current activity or activity level. For example, for the user exhibiting reduced circulation in one foot, a temperature difference between like regions on the user's left and right foot may increase as the user's activity level increases despite absence of inflammation in the user's feet. The application can therefore select or modify a threshold difference for triggering an alarm for the user in order to account such "normal" temperature changes between the user' feet.

3. System

Blocks of the method. S100 are described herein as executed by a system 100 including a left sock 110, a right sock 120, and a computer program (or "application") 130. In one variation shown in FIGS. 5 and 6, the system 100 includes: a set of left socks, wherein each left sock 110 in the set of left socks includes a left set of temperature sensors 112 and a left wireless communication module 114; a set of right socks, wherein each right sock 120 in the set of right socks includes a right set of temperature sensors 122 and a right wireless communication module 124; and an application 130 configured to execute on a computing device. In this variation, the application 130 is also configured to: access temperature data read from a left set of temperature sensors and broadcast by a left wireless communication module in a first left sock in the set of left socks during a first period of time; access temperature data read from a right set of temperature sensors and broadcast by a right wireless communication module in a first right sock in the set of right socks during the first period of time; access temperature data read from a left set of temperature sensors and broadcast by a left wireless communication module in a second left sock in the set of left socks during a second period of time succeeding the first period of time; access temperature data read from a right set of temperature sensors and broadcast by a right wireless communication module in a second right sock in the set of right socks during the second period of time; calculate a temperature difference between temperatures read from analogous temperature sensors in the left set of temperature sensors in the second left sock and the right set of temperature sensors in the second right sock; and issue a notification on a display of the computer system in response to the temperature difference exceeding a threshold difference.

In one implementation, each sock in the system 100 can also include: a garment 111 defining an internal surface and an external surface and configured to be worn on a human foot; a left set of temperature sensors 112 integrated into or otherwise arranged on the sock 110; and an anklet 119 mounted to the garment in and housing a battery, a controller 116, a proximity sensor 118, a computer-readable memory, and/or a wireless communication module 114. A left sock 110 can be labeled (e.g., with an embossed "L") or colored (e.g., entirely in black or with a black patch) to indicate that the left sock 110 is to be worn on a left foot. Similarly, a right sock 120 can be labeled (e.g., with an embossed "R") or colored (e.g., entirely in red or with a red patch) to indicate that the right sock 120 is to be worn on a right foot. When in use (e.g., when worn by a user), a pair of left and right socks can be configured to wirelessly connect or "sync" directly. Alternatively, a pair of left and right socks can wirelessly connect to a computing device executing the application 130, and the application 130 can control the left and right socks directly, or the left and right socks can communicate with each other via a wireless connection through the computing device.

Each sock can include a set of temperature sensors 112 arranged in a configuration (or "pattern") to enable collection of temperature values at multiple distinct regions of a foot placed within the sock. In one example shown in FIGS. 4 and 7, a left sock 110 includes a left set of six temperature sensors 112 arranged in a left pattern including: a first temperature sensor arranged in a first Ossa digit region of the left sock 110 and configured to face the first Ossa digit proximal the distal phalange of a user's left foot when the left sock 110 is worn by the user; a second temperature sensor, a third temperature sensor, and a fourth temperature sensor arranged along a boundary between a phalange region and a metatarsal region of the left sock 110 and configured to face the boundary of the phalanges and the metatarsals of the user's left foot when the left sock 110 is worn by the user; a fifth temperature sensor arranged along a boundary between the metatarsal region and a tarsal region of the left sock 110 and configured to face the boundary of the metatarsals and the tarsals of the user's left foot when the left sock 110 is worn; and a sixth temperature sensor arranged in a heel region of the left sock 110 and configured to face the heel of the user's left foot when the left sock 110 is worn by the user. The left sock 110 can thus include a left set of temperature sensors 112 distributed across four distinct temperature zones of the user's foot. The right sock 120 can include a right set of six temperature sensors 122 arranged in a configuration (or "pattern") that mirrors the left set of temperature sensors 112 in the left sock 110, as shown in FIGS. 4 and 7.

Each sock in the set of left and right socks can also include a proximity sensor 118, 128 configured to detect the presence of skin or a body part inside the sock and to determine that the sock is currently being worn on a user's foot based on an output of the proximity sensor. In one implementation, a sock 110 includes: an anklet 119 embedded into or installed over the exterior of the sock near the mouth of the sock and housing the controller 116; and a proximity sensor 118 defining a capacitive touch sensor facing the internal surface of the sock and mounted or integrated into the anklet 119. In one example, the proximity sensor 118 can be coupled to an interrupt pin on the controller in the sock; and the controller defaults to a sleep state in which the controller executes a minimum of processes. In this example, proximity to a massive object (e.g., a foot or a leg) can trigger a change in the output state of the proximity sensor 118, such as from a binary LO voltage to a binary HI voltage (or vice versa), which can trigger the controller to transition from the sleep state to an active state. Once in the active state, the controller can regularly sample the proximity sensor 118 to confirm placement of the sock on a user's foot, such as just before scanning the temperature sensors in the sock during a sampling period or once per ten-minute interval, as described below. Alternatively, the controller can enter the active state in response to receipt of an activation input from the computing device (e.g., from a smartphone or tablet executing an instance of the application 130). The controller can then return to the sleep state in response to a change in the output of the proximity sensor 118 to the binary LO voltage, which may indicate that a foot has been removed from the sock, or in response to a deactivation command received from the computing device.

While in the active state, a controller in a sock can scan the set of temperature sensors integrated into the sock. For example, each temperature sensor can output a temperature in the form of an analog voltage, and the controller can convert these analog voltages into digital temperature values (hereinafter "temperatures") and store these temps locally and/or transmit these temperatures to the computing device executing the application 130 in real-time or asynchronously, such as over an intermittent or persistent wireless connection.

While in use (i.e., when worn by a user), a pair of left and right socks can wirelessly connect to a local computing device executing the application 130—such as the user's smartphone, tablet, or smartwatch—and can cooperate with the application 130 to synchronize discrete slave clocks integrated into the left and right socks with a master clock maintained at the mobile computing device; once the master and slave clocks are synchronized in time, the left and right socks can implement similar sampling frequencies or sampling intervals to intermittently sample the left and right sets of temperature sensors, respectively, such that sets of temperature data generated by the left and right socks throughout use are substantially matched in time. The application 130 can then compare sets of temperature data generated by the left and right socks at substantially similar times to reject common noise and to predict possible inflammation in a particular region of a foot, across one whole foot, or in both feet of the user in Block S130, as described below. (Alternatively, the application 130 can regularly transmit prompts to the left and right socks to scan their temperature sensors and to return (e.g., wirelessly broadcast) new temperature data back to the computing device for processing by the application 130.)

Alternatively, the left sock 110 can wirelessly connect to the right sock 120, such as when the user's mobile computing device is not within wireless range of the left and right socks while in use. In this implementation, the left controller can function as a master controller, and the right controller can function as a slave controller (or vice versa). The left controller can thus actively transmit a scan command to the right sock 120 to trigger substantially simultaneous temperature scans at the left and right socks. Alternatively, the left sock 110 can synchronize its internal clock with the internal clock of the right sock 120, and the left and right socks can separately execute scan cycles to record temperatures across their respective temperature sensors.

A sock can also transmit the state of its battery to the computing device; the application 130 can thus track a charge state of the battery in the sock and prompt the user to dispose of the sock when the charge state of the battery drops below a threshold charge state, such as by rendering this prompt on a display of the computing device. When the user replaces this sock with a second sock: a proximity sensor in the second sock can wake a controller in the second sock; the controller in the second sock can trigger a wireless communication module in the second sock to broadcast a wireless connection request; and the application 130 executing on the computing device can confirm wireless connection to the second sock and download temperature data from the second sock during its use.

Socks can be provided to a user in a "kit," including multiple left socks and an equal number of right socks. For example, the kit can include seven left socks and seven right socks. The user can thus wear one left sock and one right sock in the kit during each day of each week over a period of time (e.g., six months); the user can also wash all or most socks in the kit once per week in preparation for wearing socks in the kit again the following week.

However, the application 130 (or other computer software) method can be executed by any other local or remote computing device, such as a smartphone, a tablet, a smartwatch, or a remote server. For example, upon receipt of temperature data from the left and right socks, the application 130 executing on the user's mobile computing device can upload these temperature data to a remote computer system for remote processing and analysis; the remote computer system can implement methods and techniques described herein to process these data and to return an inflammation prediction and/or prompts to the user and affiliated care providers over time. Alternatively, Blocks of the method S100 can be executed locally at one or both socks.

Blocks of the method S100 can also be executed by a computing device in conjunction with any other foot-borne device(s) or garment(s) containing one or more temperature sensors—such as slippers, shoes, or shoe or sole inserts—to collect temperatures of various regions of a user's feet and to transform these temperature data into a prediction of inflammation or other medical condition affecting one or both of the user's feet (e.g., before inflammation or an infection becomes so severe that the user risks losing the affected foot.) The foot-borne devices can also include any other type and number of temperature sensors in any other configuration for measuring temperatures across the soles of a user's feet, tops of the user's feet, the user's ankles, and/or any other regions of the user's feet or lower legs; the computing device executing the method S100 can then implement methods and techniques described below to detect inflammation or other foot- and lower-leg-related condition based on data collected through these temperature sensors.

Furthermore, Blocks of the method S100 are described herein as implemented by an application to detect or predict inflammation in a user's feet. However, Blocks of the method S100 can additionally or alternatively be implemented to detect or predict a wound (e.g., a puncture, a sore, or an ulcer), a broken bone, or other medical condition in the user's feet.

4. Baseline Temperature Difference

Block S110 of the method S100 recites, in response to receipt of confirmation of absence of inflammation in a left foot of a user and a right foot of a user at a first time, accessing a first temperature measured through a left temperature sensor at approximately the first time, wherein the left temperature sensor is arranged in a left sock worn on the left foot of the user; and Block S112 of the method S100 recites accessing a second temperature measured through a right temperature sensor at approximately the first time, wherein the right temperature sensor is arranged in a right sock worn on the right foot of the user. Furthermore, Block S120 recites calculating a baseline temperature difference as a function of a difference between the first temperature and the second temperature. Generally, during a setup routine, the application collects baseline temperature data from a pair of left and right socks worn by the user in Blocks S110 and S112 and then calculates a baseline temperature difference for the user in Block. S120, as shown in FIG. 1. In particular, in Blocks S110, S112, and S120, the application cooperates with a pair of socks worn by the user to collect temperatures across soles of the user's feet and processes these temperatures to calculate a baseline temperature difference that, given verification of the health of the user's feet, represents a "normal" or "expected" temperature difference between two like regions of the user's left and right feet.

4.1 Skin Proximity

Figure 5:
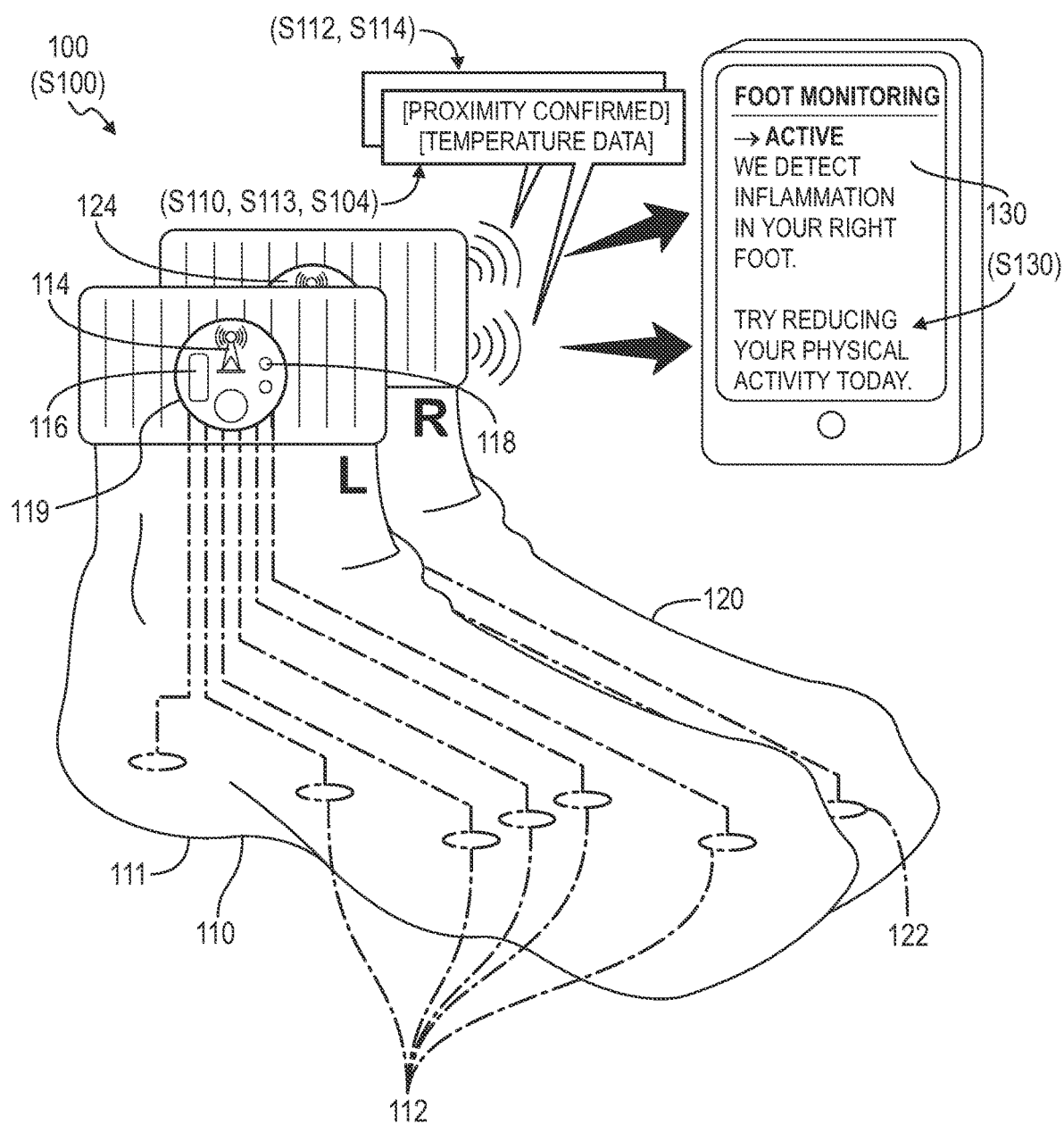
FIG. 5 is a flowchart representation of a system.
Figure 6:
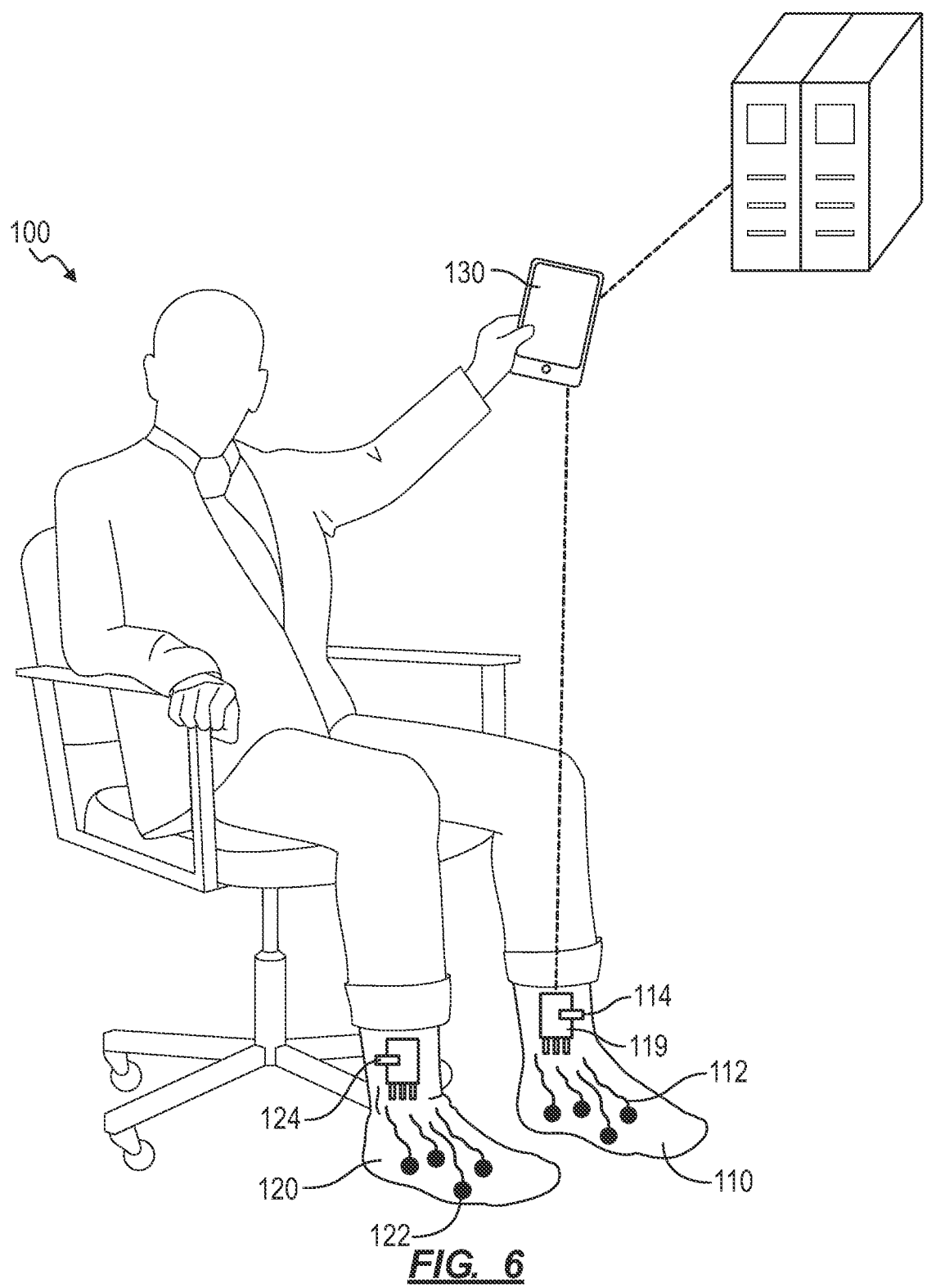
FIG. 6 is a schematic representation of one variation of the system.

As shown in FIG. 5, one variation of the method S100 further includes Block S104, which recites at the left sock: determining that the left sock is in place on a foot based on a signal output by a proximity sensor arranged in the left sock; and entering a standby mode in response to determination that the left sock has been removed from the foot. Generally, in this variation, a sock can determine its presence on a user's foot based on a signal read from a sensor integrated into the sock in Block S104, can sample temperature sensors arranged in the sock while presence on a user's foot is confirmed, and can then return to an inactive (or "sleep") state in which the temperature sensors are not sampled and in which temperature data is not broadcast to the computing device when presence on a user's foot is not detected.

In one implementation, each sock includes a proximity sensor e.g., a capacitive skin contact or capacitive proximity sensor) electrically coupled to an interrupt-enabled wake pin on a controller arranged in the sock; when the sock is placed on a user's foot, the output of the proximity sensor may change, thereby waking the controller from an inactive (e.g., low-power) state to an active state. Upon transitioning into the active state, the controller can trigger the wireless communication module to broadcast a query to connect to the computing device. Once the sock is connected to the computing device, the application—executing on the computing device—can initiate a setup routine to calculate a baseline temperature difference specific to this pair of socks or general to all socks in the kit.

Furthermore, during use, a sock can regularly sample the proximity sensor to confirm its presence on a user's foot. For example, before initiating a scan cycle to read temperatures from each temperature sensor in the sock, the controller in the sock can sample the proximity sensor to confirm that the sock is currently present on the user's foot. Once such presence is confirmed, the controller can initiate a scan cycle to record temperatures from each of its integrated temperature sensors. However, if the output of the proximity sensor indicates that the sock is no longer present on a foot, the controller can return to the inactive state. The sock can implement this process prior to executing each scan cycle, both during the setup routine and during subsequent use, as described below.

The left and right socks can additionally or alternatively include orientation sensors (e.g., accelerometers), and the left and right controllers can estimate their placement on the user's feet when outputs of these orientation sensors remain substantially similar but vary globally over time. The left and right socks can similarly include motion sensors (e.g., accelerometers, gyroscopes), and the left and right controllers can estimate their placement on the user's feet when outputs of these motion sensors remain substantially similar but vary globally over time. The left and right socks can therefore limit execution of scan cycles to periods in which both socks are in similar orientations (e.g., with respect to gravity) and experiencing similar types and degrees of motion.

4.2 Initializing Setup Routine

Once a left and right sock are placed on the user's feet and connected to the computing device, the application can initiate a setup routine to calculate a baseline temperature difference: if a baseline temperature difference has not previously been calculated for the user; if a current baseline temperature difference is outdated (e.g., the current baseline temperature difference was calculated more than three months prior); or if the left and right socks have not previously been paired (e.g., to compensate for variations in temperatures read by temperature sensors across this combination of left and right socks). During a setup routine, the application can therefore generate a baseline temperature difference general to all combinations of socks worn by the user or specific to a unique combination of left and right socks currently in place on the user's feet.

In one implementation, once the left sock, right sock, and computing device are wirelessly connected and the application confirms the charge states of the batteries in the left and right socks, the application prompts the user to confirm the health of her feet through the computing device, as shown in FIG. 1. For example, once a setup routine is initialized, the application can serve a first prompt—through a user interface on the computing device—to confirm absence of visual signs of inflammation in the left foot of the user and the right foot of the user. The user (or other person present near the user, such as a doctor or nurse) can then submit—through the user interface—confirmation of absence of visual signs of inflammation in her left and right feet. In particular, when placing the left and right socks on her feet, the user may visually inspect her feet and note visual signs of inflammation, sores, or other medical conditions; once the left and right socks have wirelessly connected to the computing device and, once the setup routine is initialized, the application can render a prompt on the display of the computing device to confirm that the user has not visually identified such inflammation, sores, or other medical conditions. In this example, the application can serve a textual foot health confirmation prompt alongside binary (e.g., "yes or no") textual responses. Alternatively, the application can: serve images of inflamed skin, foot sores, or feet with various health conditions (e.g., one image of each of a healthy foot, a foot with light inflammation and swelling, a foot with moderate inflammation and swelling, a foot with severe inflammation and swelling, and an ulcerated foot); and prompt the user to select an image that best represents each of her feet. If the user (or other person nearby) confirms that the user's feet appear healthy, the application can continue the setup routine and prepare to calculate a baseline temperature difference from temperature data collected during this setup routine.

Alternatively, the application can interface with a care provider (e.g., a doctor, a nurse), such as through a doctor portal executing on an external device, to receive confirmation that the user's feet are healthy (e.g., not inflamed, not ulcerated) and can calculate a baseline to temperature difference from temperature data collected through socks worn by the user shortly before and/or shortly after receipt of such confirmation from the care provider.

Furthermore, if the user (or care provider or other person nearby) indicates that inflammation or other health condition is present in the user's feet, the application can: note this condition; execute the methods and techniques described below to calculate a baseline temperature difference for the user's feet; determine that the condition of the user's feet is worsening if temperatures later read by left and right socks worn by the user exceed this baseline temperature difference; and determine that the condition of the user's feet is improving if temperatures later read by left and right socks worn by the user fall below this baseline temperature difference.

Figure 8:
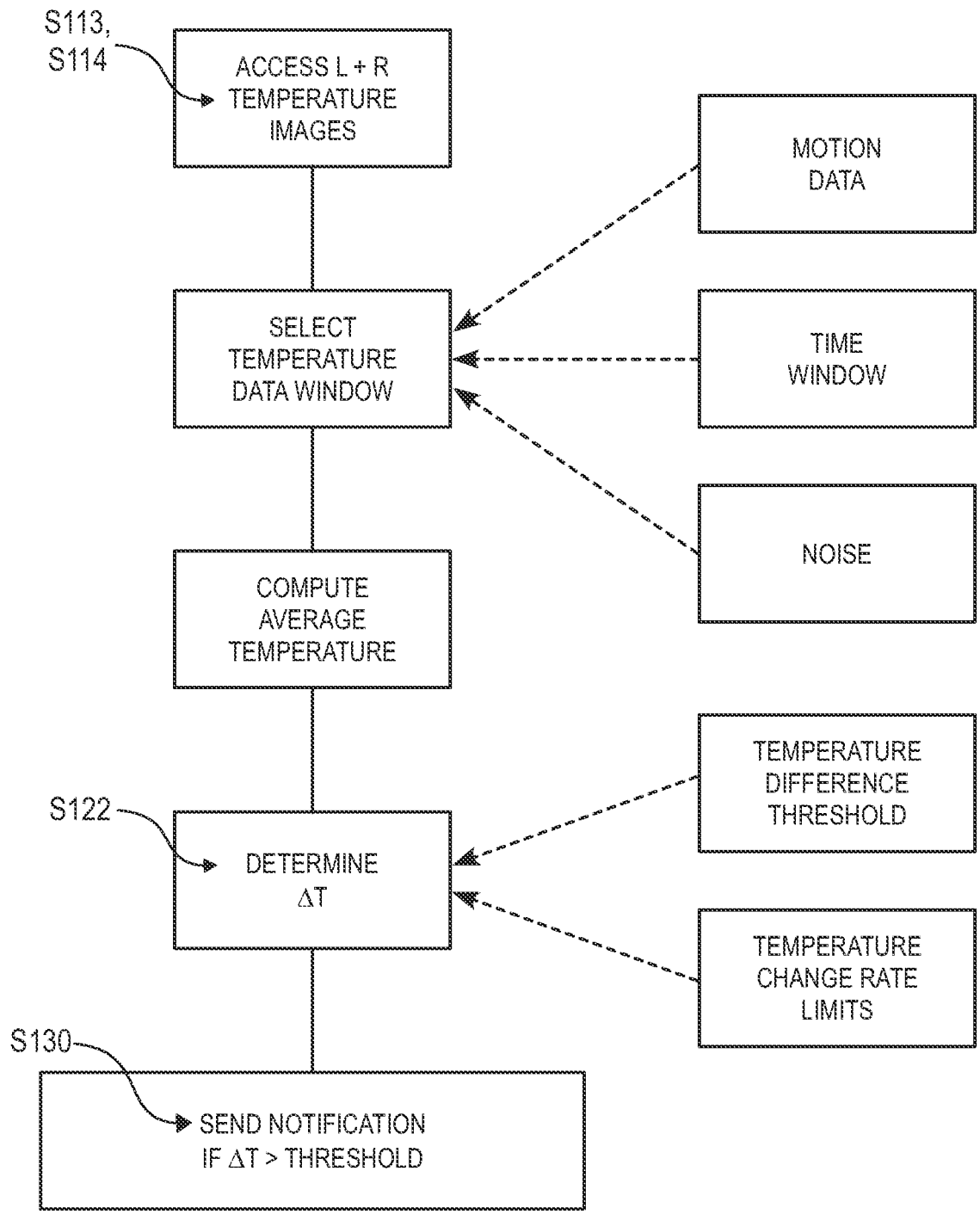
FIG. 8 is a flowchart representation of one variation of the method.

In one variation, the application serves a prompt to the user—through the user interface on the computing device—to remain sedentary throughout the setup routine in order to achieve less noise and a more consistent signal in temperatures read from temperature sensors integrated into socks currently in place on the user's feet. For example, the application can prompt the user to sit in a chair or lay down for a period of time (e.g., five minutes) while "control" temperatures are recorded through these socks in Blocks S110 and S112. Throughout the setup routine, controllers in the left and right socks can sample accelerometers and/or gyroscopes integrated into the socks and return these data to the computing device; the application can then transform these accelerometer and/or gyroscope data into a measure of the user's activity or motion level during the setup routine. Alternatively, the application can estimate the user's activity or motion level from motion data collected through an accelerometer and/or gyroscope integrated into the computing device. The application can then discard temperature data collected during periods of excess user motion during the setup period or extend the setup routine to collect additional temperature data from the socks if excess user motion is detected, as shown in FIG. 8.

4.3 Temperature Data Collection

In Block S110, the left controller in the left sock can scan the left set of temperature sensors integrated into the left sock to measure temperatures across the sole of the user's left foot and then upload these temperatures to the computing device where they are processed by the application. Similarly, in Block S112, the right controller in the right sock can scan the right set of temperature sensors integrated into the right sock to measure temperatures across the sole of the user's right foot and then upload these temperatures to the computing device where they are processed by the application.

In one implementation, throughout the setup routine, the application regularly pushes a query to the left and right socks for temperature data, such as at a rate of 1 Hz, once per minute, or once per five-minute interval. Upon receipt of such a query, the controller in the left sock can sequentially scan each temperature sensor in the left sock, populate a temperature image (e.g., an array, matrix, or other data structure) with a digital value representing an analog value read from each temperature sensor in the left sock, append each temperature image with a time of the sampling period and an identifier of the left sock, and then return this temperature image to the computing device; the controller in the right sock can implement a similar process over a substantially similar period of time in response to receipt of the same query. For example, for the left and right socks that each include six temperature sensors, as described above, the left sock can generate an temperature image that includes: [a first temperature read from the first left temperature sensor at a first time], [a second temperature read from the second left temperature sensor at the first time], [a third temperature read from the third left temperature sensor at the first time], [a fourth temperature read from the fourth left temperature sensor at the first time], [a fifth temperature read from the fifth left temperature sensor at the first time], and [a sixth temperature read from the sixth left temperature sensor at the first time]. In this example, the right sock can generate a temperature image at substantially the same time and including: [a seventh temperature read from the first right temperature sensor at the first time], [an eighth temperature read from the second right temperature sensor at the first time], [a ninth temperature read from the third right temperature sensor at the first time], [a tenth temperature read from the fourth right temperature sensor at the first time], [an eleventh temperature read from the fifth right temperature sensor at the first time], and [a twelfth temperature read from the sixth right temperature sensor at the first time], as shown in FIG. 1.

Alternatively, when the setup routine is initialized, controllers in the first and second socks can synchronize their internal clocks with the computing device (or the application); or the controller in the left sock can synchronize its internal timer directly with the internal time in the controller in the right sock. The left and right socks can then: implement a static sampling rate (1 Hz, once per minute, or once per five-minute interval); and regularly scan their integrated temperature sensors and populate a new temperature image with temperature values at each sampling period. While wirelessly connected to the computing device, the left and right socks can upload temperature images to the computing device substantially in real-time. However, if connection to the computing device is lost, the socks can store temperature images in local memory and then return these temperature images to the computing device when a wireless connection is reestablished.

Alternatively, the left and right socks can scan their temperature sensors according to a variable sampling rate. For example, the left controller can: scan the left set of temperature sensors once per hour while the user is at rest or substantially stationary, such as determined by the left controller or the application based on motion data collected locally at the left sock or at the mobile computing device; scan the left set of temperature sensors once per five-minute interval while the user is in motion (e.g., walking); and scan the left set of temperature sensors once per one-minute interval if differences between temperatures read from like temperature sensors in the left and right socks exceed a threshold difference, as described below. The right sock can implement similar methods and techniques. Similarly, the left and right socks can implement a default sampling rate (e.g., once per ten-minute interval) and implement higher sampling rates (e.g., once per ten-second or one-minute interval) responsive to commands received from the application, such as during a setup routine.

Upon receipt of temperatures from the left and right socks, such as in the form of temperature images, during the setup routine, the application can label these temperature data as control temperatures representing a baseline temperature gradient across the user's left and right feet under consistent ambient conditions. Such temperature gradients may persist across the user's left and right feet over time even under changing environment conditions (e.g., walking with socks across a cool tile floor or walking with shoes and socks across an hot asphalt road), and temperature differences between similar regions on the user's left and right feet may similarly persist even while the user's feet are healthy or remain in substantially the same condition following the setup routine. Therefore, given confirmation that the user's feet are in healthy or adequate condition, the application can label these temperature data as control temperatures and process these control data to calculate a general baseline temperature difference (or region-specific baseline temperature differences) for the user's feet. In particular, the application can later compare temperature gradients measured across the user's feet to the baseline temperature difference(s) to identify a change in the condition or health of the user's feet in Block S130, as described below.

4.4 Calculating the Baseline Temperature Difference: One-to-One

In one implementation shown in FIGS. 1 and 7, the application retrieves a pair of temperature images—including a left temperature image received from the left sock and a right temperature image received from the right sock and tagged with the same or similar (e.g., nearest) timestamps. The application then subtracts the left temperature image from the right temperature image to calculate a temperature difference image containing baseline temperature differences read from left and right temperature sensors in the left and right socks.

The application can repeat the foregoing process for other pairs of temperature images received from the left and right socks and tagged timestamps of other sampling periods during the setup routine to calculate multiple temperature difference images. The application can then linearly combine (e.g., average) these temperature difference images to calculate a final baseline temperature difference image containing baseline temperature differences between like regions on the user's left and right feet.

Therefore, the application can collect temperature data over multiple sampling periods during a setup routine and can merge these data to generate a generic baseline temperature difference, multiple temperature-sensor-specific baseline temperature differences, or multiple temperature-sensor-cluster-specific baseline temperature differences. For example, the application can cooperate with the left and right socks recently placed on the user's feet to: execute a one-minute setup routine; to execute one scan cycle at each sock once per six-second interval; calculate ten temperature differences from temperatures read from each pair of like temperature sensors in the left and right socks during the setup routine; calculate an average of the temperature differences for each pair of like temperature sensors; and store this average as the baseline temperature difference for each corresponding pair of like temperature sensors in the left and right socks given confirmation provided by the user that no inflammation is currently present in the user's feet. In this implementation, the application can calculate an average or other linear combination of temperatures read from one or more temperature sensors in the left sock over a limited time window, such as ten seconds, one minute, 20 minutes, one hour, one day, or one week and then compare an average or linear combination of temperatures read from a like set of temperature sensors in the right sock over a similar time window.

The application can implement similar methods and techniques to calculate a baseline temperature difference for a single pair of like temperature sensors in the left and right socks or for any other number of temperature sensor pairs in the left and right socks.

4.5 Calculating the Baseline Temperature Difference: Group-to-Group

In another implementation, the application merges temperatures read from like clusters of temperature sensors in the left and right socks and calculates a baseline temperature difference from differences between these merged or "composite" temperature values. For example, the application can: calculate a left average for all temperature values in a left temperature image generated at a first time; calculate a right average for all temperature values in a right temperature image generated at approximately the first time; calculate a difference between the left and right averages; and store this difference as the baseline temperature difference. The application can implement similar methods and techniques to calculate baseline temperature differences for subsets of temperature sensors in the left and right socks based on averages or other linear combinations of temperatures read from these temperature sensors in the left and right socks during the setup routine.

In another implementation, the application: calculates a first temperature difference between two temperatures within a first temperature image received from the left sock; calculates a second temperature difference between two corresponding temperatures within a second temperature image of a right foot; and then calculates a baseline temperature difference for these two pairs of temperature sensors by subtracting the first temperature difference from the second temperature difference (or vice versa). For example, the application can: calculate a left temperature difference between the first Ossa digit of a left foot and the heel of the user's left foot (i.e., by calculating a temperature difference between a first temperature sensor arranged in the first-Ossa region of the left sock and a sixth temperature sensor arranged in the heel of the left sock); calculate a right temperature difference between the first Ossa digit of a right foot and the heel of the user's right foot; and then calculate the baseline temperature difference for the first-Ossa and heel regions of the user's feet by subtracting the left temperature difference from the right temperature difference (or vice versa) in order to normalize temperature data collected from the user's left and right feet for differences in blood circulation in the user's feet, which may affect absolute temperatures of the user's first Ossa digits and heels. Later, the application can: recalculate these left and right temperature differences based on new temperature images received from the left and right socks; calculate a global difference between these left and right temperature differences; and predict a sore or inflammation on the first Ossa digit of the user's left foot if this global difference exceeds the baseline temperature difference by more than a threshold difference (e.g., a generic threshold difference or a threshold difference specific to the first Ossa digit, as described below). The application can implement similar methods and techniques to calculate temperature differences between other combinations of sensor locations on the user's left foot, to calculate temperature differences between other combinations of sensor locations on the user's right foot, and to calculate baseline temperature differences specific to various groups of clusters of temperature sensors in the left and right socks.

Once one or more baseline temperature differences are calculated in Block S120, the application can exit the setup routine and begin regular monitoring of the user's feet based on temperatures (e.g., temperature images) received from the left and right socks. Furthermore, when the user later replaces the left and right socks with another pair of left and right socks in the kit, the application can retrieve the baseline temperature difference generated during the setup routine described above and implement this baseline temperature difference to detect inflammation in the user's feet based on temperature data received from the second pair of socks. Alternatively, the application can execute a second setup routine to calculate a new baseline temperature difference for the second pair of socks before beginning to monitor the user's feet based on temperature data received from the second pair of socks.

5. Foot Monitoring

Block S113 of the method S100 recites accessing a third temperature measured through the left temperature sensor at a second time succeeding the first time; Block S114 of the method S100 recites accessing a fourth temperature measured through the right temperature sensor at approximately the second time; and Block S122 of the method S100 recites calculating a second temperature difference as a function of a difference between the third temperature and the fourth temperature in Block S122. Generally, the application: retrieves temperature data from left and right socks worn by the user in Blocks S113 and S114, respectively; and calculates temperature differences between these temperature data in Block S122 prior to predicting inflammation or another medical condition in the user's feet if these temperature differences exceed one or more corresponding baseline temperature differences by more than a threshold difference, as described below, and as shown in FIGS. 1, 2, 3, and 4.

In particular, in Blocks S113 and S114, the application can cooperate with left and right socks currently in place on the user's feet to collect temperatures (e.g., in the form of temperature images) of the soles of the user's left and right feet at similar times over a sequence of sampling periods. For example, once synchronized in time, the left and right socks can each generate one temperature image per sampling period and can upload these temperature images to the computing device as soon as a wireless connection is established with the computing device. The application can then implement methods and techniques described above to calculate temperature differences between these temperatures, such as temperature differences between temperatures read from like (i.e., mirrored) temperature sensors in the left and right socks during one sampling period.

Similarly, the application can then implement methods and techniques described above to calculate: temperature differences between average temperatures read from like clusters or groups of temperature sensors in the left and right socks; or temperature differences between an average temperature read from all temperature sensors in the left and right socks during one sampling period. For example, at approximately a first time during a monitoring period, the application can: retrieve a first temperature from a left temperature sensor arranged in an Ossa region of the left sock; retrieve a second temperature from a second left temperature sensor arranged along a boundary between a phalange region and metatarsal region of the left sock; retrieve a third temperature from a right temperature sensor arranged in an Ossa region of the right sock; retrieve a fourth temperature from a second right temperature sensor arranged along a boundary between a phalange region and metatarsal region of the right sock. In this example, the application can then calculate a left average of the first temperature and the second temperature, calculate a right average of the third temperature and the fourth temperature, and then calculate a difference between the left average and the right average before comparing this temperature difference to the baseline temperature difference to predict inflammation in the user's feet.

In another example, the application can calculate a first average temperature of the second, third, and fourth temperatures in a left temperature image (e.g., representing temperatures across the boundary of the phalanges and the metatarsals of the user's left foot during a particular sampling period) received from the left sock and subtract the first average from a second average of the second, third, and fourth temperatures in a right temperature image (e.g., representing temperatures across the boundary of the phalanges and the metatarsals of the user's right foot at the particular time) received from the right sock before comparing this temperature difference to a baseline temperature difference specific to the boundary of the phalanges and the metatarsals to predict inflammation along the boundary of the phalanges and the metatarsals of the user's feet. The application can therefore calculate a temperature difference between single, average, and composite temperatures of two or more like regions of the user's left and right feet at similar instances in time in Block S122.

The application can therefore calculate a temperature difference between temperatures read from temperature sensors at mirrored positions within the left and right socks at similar e.g., substantially identical) times; the application can then store these temperature differences—calculated from temperature images recorded during one sampling period—in a difference image (e.g., an array, a matrix) tagged with a timestamp of the sampling period.

6. Alarm: Inflammation Detection

The application can then predict inflammation in (or otherwise a change in the status of) one or both of the user's feet if a temperature difference calculated from temperature data recorded during a monitoring period exceeds the baseline temperature difference by more than a threshold difference. For example, the application can compare temperature differences—stored in a difference image generated from data recorded during a sampling period—to the baseline temperature difference and the threshold difference to predict inflammation in the user's feet.

6.1 Threshold Difference

In one implementation shown in FIG. 1, the application implements a single preset static threshold difference, such as 2.0° Celsius (3.6° Fahrenheit), and predicts inflammation in any region of one or both of the user's feet if a temperature difference calculated from temperature data collected from adjacent temperature sensors in the left and right socks during the monitoring period exceeds the baseline temperature difference by this preset static threshold difference.

Alternatively, the application can implement various threshold differences specific to select regions of a human foot (i.e., specific to temperature differences calculated from temperature data read through temperature sensors in select regions of the left and right socks). For example, the application can apply: a threshold difference of 2.8° C. to temperatures of first Ossa digits (e.g., to a temperature difference calculated from temperature data received from the first temperature sensors in the left and right socks); a threshold difference of 2.4° C. to temperatures along the phalange-metatarsal boundaries (e.g., to a temperature difference calculated from temperature data received from the second, third, fourth, and fifth temperature sensors in the left and right socks); and a threshold difference of 2.0° C. to temperatures at the heels (e.g., to a temperature difference calculated from temperature data received from the sixth temperature sensors in the left and right socks). The application can retrieve these threshold differences from a lookup table or other database stored locally at the mobile computing device or remotely, such as at a remote server or in a remote database.

In another example, the application can apply a threshold difference of 2.5° C. between [a temperature difference between a first Ossa digit and a heel on the user's left foot] and [a temperature difference between a first Ossa digit and a heel on the user's right foot] to predict inflammation in either the user's left or right toes. Similarly, the application can apply a threshold difference of 2.0° C. between [the average of temperatures across the phalange-metatarsal boundary of the user's left foot] and [the average of temperatures across the phalange-metatarsal boundary of the user's right foot] to predict inflammation in the phalange-metatarsal boundary of one of the user's feet.

In another implementation, the application can select a general or location-specific threshold difference based on the user's activity level. For example, during a monitoring period, the application can collect motion data through sensors integrated into the left and/or right socks or integrated into the computing device and then transform these motion data into an activity level of the user during the monitoring period. In this example, the application can adjust the threshold difference directly proportional to the user's activity level, such as by shifting the threshold difference along a spectrum between. 1.5° C. and 3.5° C. proportional to the user's activity level. In this implementation, the application can also persist a threshold difference over a dwell period (e.g., thirty minutes) following a decrease in the user's activity level.

6.2 Presence and Location of Inflammation

As shown in FIG. 1, for a temperature difference calculated from temperature data received from the left and right socks during one sampling period, the application can: subtract a corresponding baseline temperature difference from the temperature difference to calculate a real change in the temperature difference between corresponding regions of the user's feet; predict inflammation in a corresponding region of the user's left foot if the real change is positive in value and the absolute value of the real change exceeds the corresponding difference threshold; and predict inflammation in a corresponding region of the user's right foot if the real change is negative in value and the absolute value of the real change exceeds the corresponding difference threshold. The application can repeat this process for temperature difference represented in a difference image for the sampling period to predict inflammation across various regions of the user's left and right feet.

The application can therefore predict inflammation in specific regions of the user's left and right feet. For example, at approximately a first time the application can: retrieve a first temperature from a first left temperature sensor arranged in an Ossa region of the left sock; retrieve a second temperature from a second left temperature sensor arranged along a boundary between a phalange region and metatarsal region of the left sock; retrieve a third temperature from a first right temperature sensor arranged in an Ossa region of the right sock; access a fourth temperature from a second right temperature sensor arranged along a boundary between a phalange region and metatarsal region of the right sock; calculate a first temperature difference by subtracting the second temperature from the first temperature; calculate a second temperature difference by subtracting the fourth temperature from the third temperature; and predict inflammation local to an Ossa digit on the user's left foot—but not occurring in or occurring to a lesser degree in the phalange and metatarsal regions of the user's left foot—if the first temperature difference differs from the baseline temperature difference by more than the threshold difference, the first temperature exceeds the third temperature, and the second temperature difference differs from the baseline temperature difference by less than the threshold difference. The application can then issue an alarm or alert accordingly, such as by generating an electronic notification containing a prompt to visually inspect the first Ossa digit on the user's left foot and then serving the electronic notification through the mobile computing device executing the application, as described below. The application can implement similar methods and techniques to predict inflammation in other distinct regions of the user's feet and to respond accordingly.

The application can also merge multiple temperature differences calculated from two temperature images into a map or gradient of inflammation in the user's feet. In the foregoing example, the application can interpret a relatively large deviation between the first temperature difference and the baseline temperature, a relatively moderate deviation between the second temperature difference and the baseline temperature, a relatively small deviation between a third temperature difference—corresponding to temperatures in the heels of the user's left and right feet—and the baseline temperature, and the first temperature that exceeds the third temperature as inflammation centered in and radiating outwardly from the user's left toes. Similarly, the application can interpret a relatively moderate deviation between the first temperature difference and the baseline temperature, a relatively large deviation between the second temperature difference and the baseline temperature, a relatively small deviation between the temperature difference and the baseline temperature, and the third temperature that exceeds the first temperature as inflammation centered in the user's left foot (e.g., proximal the phalange-metatarsal boundary) and radiating outwardly toward the user's toes and heel. The application can therefore confirm a prediction of inflammation in one region of the user's feet based on increased temperature differences between nearby regions of the user's feet and identify a highest-risk region or a region of greatest inflammation based on such temperature gradients across the user's feet.

6.3 Inflammation Detection Over Time

Figure 3:
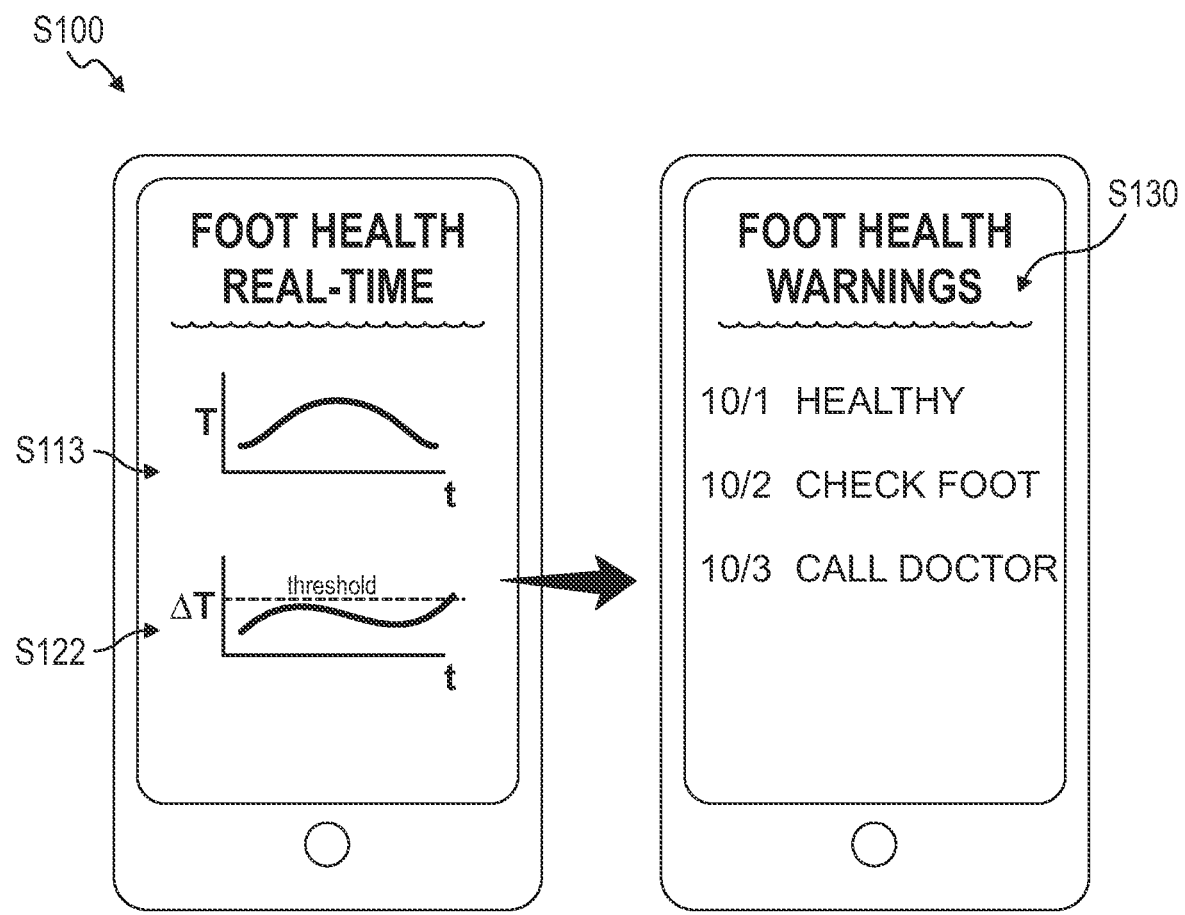
FIG. 3 is a flowchart representation of one variation of the method.

The application can implement the foregoing methods and techniques for a set of temperature images recorded over a sequence of sampling periods and predict inflammation in a particular region of the user's feet based on these temporal temperature differences, as shown in FIG. 3.

In one implementation, the application predicts inflammation in a particular region of the user's foot if all temperature differences—calculated between a left temperature sensor and a right temperature sensor arranged in corresponding locations in the left and right socks over a monitoring period of threshold duration (e.g., five minutes, one hour)—exceed the threshold difference. Similarly, the application can predict inflammation in a particular region of the user's foot if a threshold proportion (e.g., 80%) of all temperature differences—calculated between a left temperature sensor and a right temperature sensor arranged in corresponding locations in the left and right socks over a monitoring period of threshold duration (e.g., one hour, two hours exceed the threshold difference. In one example, the application: accesses a first temperature and a second temperature measured through a first left temperature sensor and a first right temperature sensor at a first time; accesses a third temperature and a fourth temperature measured through the first left temperature sensor and the first right temperature sensor at a second time succeeding the first time by a threshold duration; calculates a first temperature difference as a function of a difference between the first temperature and the second temperature; and calculates a second temperature difference as a function of a difference between the fifth temperature and the sixth temperature. In this example, the application can then issue an alarm, as described below, if both the first temperature difference and the second temperature difference differ from the baseline temperature difference by more than the threshold difference.

In this implementation, the application can repeat the foregoing processes upon receipt of temperature data from the left and right socks following each scan cycle to identify temperature differences that differ from the baseline temperature difference by more than a threshold difference and to then predict inflammation in a particular region of the user's feet when such temperature differences occur consecutively over a minimum period of time or in sufficient proportion. Once the application develops such a prediction, the application can prompt the user (or a care provider) to address this prediction in Block S130, as described below.

In another implementation, the application: generates a virtual chart; populates the virtual chart with temperature differences less the baseline temperature difference calculated from temperature data read from a particular pair (or group) of temperature sensors in the left and right socks throughout a current monitoring period or throughout multiple discrete monitoring periods (e.g., one contiguous monitoring period per day for the last seven days); and characterizes data contained in the virtual chart, such as by calculating a trend line that best fits data contained in the virtual chart. The application can then predict inflammation in a region of the user's left foot corresponding to this pair of temperature sensors if a section of the trend line exceeding the threshold difference exhibits a positive slope. In this implementation, the application can also predict a severity or risk of this inflammation to the user's left foot proportional to the magnitude of the slope of the trend line. Similarly, the application can predict inflammation in a region of the user's right foot corresponding to the location of the pair of temperature sensors in response to the trend line exhibiting a negative slope; and the application can predict a severity or risk of this inflammation in the user's right foot proportional to the magnitude of the slope of the trend line. However, if the slope of the trend line remains at approximately null, the application can determine that the condition of the corresponding region of the user's foot is not substantially changing. Similarly, if the trend line remains within positive and negative threshold difference hounds, the application can predict little or no inflammation in the user's feet.

In a similar example shown in FIG. 2, the application: generates a virtual chart; plots a first set of temperatures read from a temperature sensor in the left sock over a series of scan cycles on the virtual chart; and plots a second set of temperatures read from a like temperature sensor in the right sock over the same series of scan cycles on the virtual chart. In this example, the application can then: predict inflammation in one of the user's feet if the first and second trend lines diverge; and calculate a probability that such inflammation is present in the user's feet proportional to a rate of this divergence between the first and second trend lines. Therefore, if the first and second trend line remain substantially parallel over time, such as over multiple hours or days, the application can predict that the state of the user's feet is not significantly changing. (If the first and second trend lines remain parallel but significantly offset in temperature over time, the application can also predict poor blood circulation in the user's foot corresponding to lower overall temperature.)

The application can implement similar methods and techniques to track and analyze trends in average or composite temperatures differences calculated from temperatures read from a cluster or group of temperature sensors in the left and right socks.

Therefore, by tracking changes in temperature differences for each pair of corresponding temperature sensors or groups of temperature sensors in the left and right socks over time, the application can reduce false positives and reject noise occurring in the system 100 over short time scales, such as due to sensor drift or due to changes in ambient conditions. In particular, because an infection or other medical condition in a user's feet may progress over a relatively long period of time, such as over multiple hours or over multiple days, the application can transform trends in temperature differences read from like temperature sensors or like groups of temperature sensors over time (e.g., two hours) into a prediction of inflammation in a particular region of the user's feet (and a severity of this inflammation), thereby reducing false positives and false negatives substantially without increasing risk to the user due to excessive delay in treatment.

6.4 Inflammation Probability

In another implementation, the application can transform a difference between a temperature difference and a baseline temperature difference directly into a probability that the user is experiencing inflammation in one of her feet. For example, if a temperature difference—calculated as described above—differs from the baseline temperature difference by 1° C., the application can predict a 10% chance that the user is experiencing inflammation in one of her left and right feet. However, in this example, if the temperature difference differs from the baseline temperature difference by 2.0° C., the application can predict a 50% chance that the user is experiencing inflammation in this foot. Therefore, as in this example, the application can calculate a probability of occurrence of inflammation in the user's feet directly proportional to a difference between a temperature difference—calculated from temperature data recorded during a monitoring period—and a baseline temperature difference.

Similarly, the application can calculate a probably of inflammation in the user's feet based can a temperature difference calculated from temperature data recorded over a sequence of sampling periods. For example, the application can compare two sequential temperature differences (e.g., a first temperature difference calculated from a first pair of temperature images recorded during a first sampling period and a second temperature difference calculated from a second pair of temperature images recorded during a second sampling period following the first sampling period) to a threshold difference. In this example, if the difference between the first temperature difference and the baseline temperature difference is 2.0° C. and the difference between the second temperature difference and the baseline temperature difference is 1° C., the application can identify a trend in temperature differences back toward the baseline temperature difference and calculate a 5% probability that the user is experiencing inflammation (or other medical condition) in her feet accordingly. However, if the difference between the first temperature difference and the baseline temperature difference is 2.0° C. and the difference between the second temperature difference and the baseline temperature difference is also 2.0° C., the application can determine that such temperature difference excess over the baseline temperature difference is persistent and calculate a 50% probability that the user is experiencing inflammation in one of her feet accordingly. Furthermore, if the difference between the first temperature difference and the baseline temperature difference is 2.0° C. and the difference between the second temperature difference and the baseline temperature difference is also 2.5° C., the application can identify a trend in increasing temperature differences over the baseline temperature difference and calculate a 90% probability that the user is experiencing inflammation in one of her feet accordingly.

The application can therefore calculate an increasing probability of inflammation in the user's feet as additional temperature differences—between temperatures read from two like temperature sensors in the left and right socks—exceeding the baseline temperature difference by more than the threshold difference are calculated over time. Similarly, the application can calculate an increasing probability of inflammation in the user's feet directly proportional to an upward trend in differences between temperature differences—between temperatures read from two like temperature sensors in the left and right socks—and the baseline temperature difference.

6.5 Trends

In one implementation, the application can correlate a trend in increasing temperature difference between temperatures read from like temperature sensors in the left and right sock occurring over an extended period of time (e.g., eight hours) with an infection in this region of one of the user's feet. The application can also correlate [a trend in increasing difference between the average temperature of the user's left foot and the average temperature of the user's right foot] occurring simultaneously with [a temperature gradient across the user's left foot indicating reduced temperatures in the user's left toes over time] with reduced circulation in the user's left toes. Furthermore, the application can correlate [an increasing difference in composite temperature across the phalange-metatarsal boundary of the user's left and right feet] occurring simultaneously with [reduced temperature of the first Ossa digit in the user's right foot] with pes planus in the user's right foot. However, the application can implement and correlate any other trends or combination of trends in temperature changes across one or both of the user's feet with any other medical condition in any other way.

The application can also access and implement a foot condition model, as shown in FIG. 1, defining relationships between trends in temperature changes and various medical conditions (e.g., foot ulcers, athlete's foot, nail infections, poor blood circulation, or hammertoe). The application can thus compare real trends in temperatures across the user's feet over time to the foot condition model to predict a foot condition in the user's feet and to calculate a probability that this foot condition is present.

The application can therefore implement methods and techniques described above to predict a particular medical condition—such as a foot ulcer, athlete's foot, nail infection, poor blood circulation, hammertoe, or other foot-related medical condition—occurring in one or both of the user's feet based on temperature differences between temperatures read from two or more like temperature sensors in the left and right socks.

6.6 False Positive Rejection

In one implementation shown in FIG. 8, the application can calculate a rate of change in temperature differences read from a pair a group) of temperature sensors in the left and right socks over time and can discard relatively high temperature differences if these increasing temperature differences occurred relatively rapidly (e.g., over a short period of time). In particular, the application can associate increases in temperature differences read from two like temperature sensors in the left and right socks: with increasing inflammation in a corresponding region of the user's feet if this increase occurs over a relatively long time scale; and with a change in ambient conditions near the user's feet (and not increasing inflammation in the user's feet) if this increase occurs over a relatively short time scale. For example, if while wearing shoes over a left sock and a right sock from the kit, the user steps from standing in grass to standing with her left foot in a patch of grass and her right foot on an hot asphalt driveway, the application can detect a rapid rise in temperature at the user's right foot relative to the user's left foot. In another example, once the user sits beside a fire with her right foot nearer the fire than her left foot, the application can detect a rapid rise in temperature at the user's left and right feet and a greater increase in temperature at the user's right foot. However, because increasing temperature differences thus calculated by the application occur over relatively short periods of time (e.g., more than 1° C. per five-minute interval), the application can associate these increasing temperature differences with external factors and without alarms responsive to these increasing temperature differences.

Therefore, in this implementation, the application can: access a first temperature measured through the left temperature sensor at a first time; access a second temperature measured through the right temperature sensor at approximately the first time; access a third temperature measured through the left temperature sensor at a second succeeding the second time; access a fourth temperature measured through the right temperature sensor at approximately the second time; calculate a first temperature difference as a function of a difference between the first temperature and the second temperature; calculate a second temperature difference as a function of a difference between the third temperature and the fourth temperature; calculate a rate of temperature from the first time to the second time change based on a difference between the first temperature difference and the second temperature difference and a duration of time between the first time and the second time; and then withhold an alarm responsive to the first and second temperature differences differing from the baseline temperature difference by more than the threshold difference if the rate of temperature change exceeds a threshold rate of change.

In this implementation, the application can return to normal operation once absolute temperatures read from temperature sensors in the left and right socks return to a predefined "normal" temperature window (e.g., between 35° C. and 38° C.).

6.7 Cross-Sock Pair Baseline Temperature Difference

As described above, the application can apply a baseline temperature difference (or a set of temperature-sensor-region-specific baseline temperatures) calculated from data collected by a first left sock and a first right sock in the kit to other pairs or combinations of left and right socks worn by the user during subsequent monitoring periods. For example, a first left sock can detect (e.g., regularly confirm) its placement on a foot (e.g., on the user's left foot) and a first right sock can detect its placement on a foot (e.g., the user's right foot) over a first period of time (e.g., a first day) spanning the setup routine and a first monitoring period. The application can then implement methods and techniques described above to calculate one or more baseline temperature differences froze data collected from the first left sock and first right sock during the first period of time. Over a second period of time succeeding the first period of time (e.g., the next day), a second left sock—in the kit—can detect (e.g., regularly confirm) its placement on a foot (e.g., the user's left foot), and a second right sock—in the kit—can confirm its placement on a foot (e.g., the user's right foot) of the user. During the second period of time, the application can: access a third temperature measured through a second left temperature sensor arranged in the second left sock (e.g., at a third time in the second period of time); access a fourth temperature measured through a second right temperature sensor arranged in the second right sock (e.g., at approximately the third time); calculate a second temperature difference between the third temperature and the fourth temperature; implement methods and techniques described above to predict inflammation in one of the user's feet if the second temperature difference differs from the baseline temperature difference by more than the threshold difference; and then issue an alarm accordingly, as described below.

6.8 Sampling Rate Controls

The application can also dynamically adjust a sampling rate implemented by left and right socks worn by the user during a monitoring period based on predicted presence and/or extent of inflammation in the user's feet. For example, the left and right socks can implement a default sampling rate of one sampling period per ten-minute interval during a monitoring period; in response to prediction of inflammation in one of the user's feet based on temperature data received from the left and right socks during the monitoring period, the application can transmit a command to the left and right socks to execute scan cycles at an increased sampling rate of once per minute. The left and right socks can then execute scan cycles and return temperature data to the computing device at this revised sampling rate. Once the application determines that temperature differences between the user's feet are diminishing or that the predicted inflammation in the user's feet was incorrect based on temperature data received at this increased rate, the application can push a command to the left and right socks to return to the default sampling rate.

In another implementation, the application can receive a request for current foot temperatures from the user through the user interface and then push a query for temperature data to the left and right socks. Upon receipt of these temperature data from the left and right socks, the application can present these temperature data to the user through the user interface, as described below.

6.9 Template Matching

In another implementation, the application accesses a set of predefined template images, each containing temperature data representative of a known foot condition (and labeled with a probability for this condition). The application can then implement template matching techniques to match: a temperature image generated from temperature data received from one sock; a difference image generated by subtracting a left temperature image from a right temperature image (or vice versa); or a composite temperature image generated by fusing temperature data in one or more temperature images; etc. to a nearest temperature image. The application can then predict occurrence of the foot condition—associated with the matched template image—in the user's feet.

The application can thus match temperature images or difference images generated from temperature data received from the left and right socks to a particular template image—in a set of template images—labeled with a known medical condition (e.g., foot ulcers, athlete's foot, nail infections, poor blood circulation, or hammertoe) to predict occurrence of such a medical condition in the user's feet.

6.10 Single Foot Inflammation Detection

In one variation, the application implements similar methods and techniques to: track temperatures at one region of one of the user's feet over time; detect an upward trend in the temperature of this region of the user's foot over a relatively long time scale (e.g., a 12-hour period); and issue an alarm given an upward trend in temperature of this foot region over this period of time. In particular, rather than compare temperatures between like regions of the user's left and right feet, the application instead tracks the temperature in this region of the user's left foot (or right foot) independently of the user's right foot (or left foot) and predicts inflammation in this region of the user's left foot responsive to an upward trend in temperatures of this region of the user's left foot. Because the user may wear a temperature-sensing-enabled sock on her left foot continuously (i.e., uninterrupted) over an extended period of time exceeding eight, twelve, or even eighteen hours in duration, the application can regularly collect temperature data of the user's left foot from this left sock over this extended period to time. For example, the sock can sample its integrated temperature sensors once per five-minute interval; the application can thus a mass roughly 96, 144, or 216, temperature values over such a period of time. By calculating a best-fit line or other trend line across these temperatures, the application can determine whether the temperature in the corresponding region of the user's foot is: increasing, which may indicate inflammation; decreasing, which may indicate healing; or constant, which may indicate a healthy foot or steady-state. Furthermore, the application can predict an aggressiveness of such inflammation or a risk of this inflammation to the user based on a slope of this best-fit line.

As described above, the application can also label temperatures received from one sock as representative of a healthy foot based on confirmation of foot healthy received from the user or related entity. The application can then predict inflammation in one of the user's feet given a trend away from a "healthy" or baseline temperature in this foot over time. For example, if the temperature of a region of the user's foot trends downward from a "healthy" or baseline temperature, the application can predict reduced blood flow to this region of the user's foot; however if the temperature of this region of the user's foot trends downward from a unhealthy or elevated temperature, the application can determine that the user's foot is healing.

The application can also implement methods and techniques described above to compare temperatures of different regions of one of the user's feet to predict inflammation in one of these regions. For example, for each sampling period, a temperature-sensing-enabled sock worn on the user's left foot can record six temperatures of six discrete regions of the user's left foot and transmit these to the computing device. The application can calculate a linear combination (e.g., an average) of these six temperatures and store this value as a baseline temperature. The system can then compare the temperature of each of these regions to the baseline temperature and predict inflammation in a particular region of the user's left foot if a temperature of this particular region exceeds the baseline temperature by more than the threshold temperature difference, as described above. The application can recalculate a baseline temperature for each sampling period, can implement methods and techniques described above to track temperature deviation from this baseline temperature over time, and can predict inflammation in the user's left foot accordingly. The application can implement similar methods and techniques to independently predict inflammation in the user's right foot.

However, the application can implement any other method or technique to predict inflammation in one of the user's feet from temperature data collected from this foot independent of temperature data collected from the user's other foot. For example, the application can implement such methods or techniques to detect inflammation in the foot of a user with a foot amputation.

7. Notifications

Block S130 of the method S100 recites, in response to the second temperature difference differing from the baseline difference by more than a threshold difference, issuing an alarm through the user interface. Generally, in Block S130, the application executing on the user's mobile computing device (or other local or remote computing device or computer system) generates a notification indicating possibility of inflammation in the user's feet, such as in a particular foot or in a particular region of a particular foot, and then serves this notification to the user and/or to a care provider affiliated with the user, as shown in FIGS. 1-5. For example, the application can: notify the user exclusively of a relatively small temperature difference between her left and right feet that may suggest minor inflammation; notify the user and her family member of a moderate temperature difference between her left and right feet that may suggest moderate inflammation; and notify the user, her family member, and a care provider (e.g., a doctor, a nurse) of a relatively large temperature difference between her left and right feet that may suggest significant inflammation or diabetic ulceration in her feet.

7.1 Visual Inspection

In one implementation shown in FIG. 1, in response to calculation of a binary prediction of inflammation in one of the user's feet (e.g., in response to a temperature difference that exceeds the baseline temperature difference by more than the threshold difference) and/or calculation of a probability of inflammation in the user's feet that exceeds a preset threshold probability (e.g., 65%), the application generates a prompt to manually inspect the user's feet for inflammation, sores, ulcers, infections, or other medical conditions and serves this prompt to the user or to a related entity through the user's mobile computing device or through another related computing device. In this implementation, when generating the prompt, the application can: retrieve a virtual representation (e.g., a digital image) of a left foot adjacent a right foot; encircle, highlight, color, or otherwise visually demarcate a particular region of a particular foot predicted to exhibit inflammation or associated with a greatest probability of infection; insert this virtual representation and a prompt to inspect the indicated foot region into the prompt; and then serve the prompt to the user, such as by rendering the prompt in notification form on a display of the computing device. Similarly, the application can calculate temperature gradients across the soles of the user's left and right feet based on temperature images received from left and right socks during a recent sampling period or calculated by averaging or extrapolating temperature gradients froze temperature images received from the left and right socks over a period of time; the application can then map or project these temperature gradients onto the virtual representation of the user's left and right feet and color the virtual representation accordingly in order to visually indicate to the user the predicted location and severity of inflammation across the user's feet.

The application can also selectively push a prompt to manually inspect the user's feet to the user and/or other related entities. For example, if the application calculates a 30% or greater probability that a region of one of the user's feet is exhibiting inflammation (e.g., medically-risky inflammation), the application can generate a notification prompting the user to manually inspect her feet and then serve this notification to the user via the user's mobile computing device in Block S130. (The application can additionally or alternatively generate an email, text message, or other digital notification and serve this notification to the user through a corresponding electronic account in Block S130.) Furthermore, if the application calculates a 75% or greater probability of inflammation in the user's feet, the application can implement similar methods and techniques to additionally notify a doctor, nurse, or other care provider affiliated with the user of a likely presence of inflammation in the user's feet, such as via email or other electronic notification. In this example, if the application calculates a 95% or greater probability of inflammation in the user's feet and such probability of inflammation has persisted for a threshold period of time (e.g., 48 hours), the application can automatically notify emergency medical services of a medical risk to the user, such as via an automated phone call or via email.

The application can therefore prompt a user (and/or other related entities) to visually inspect her feet for signs of inflammation (or other medical conditions). The application can also prompt the user (or other entity) to provide confirmation that inflammation is or is not present (e.g., not visually or tactilely noticeable) in one or both of the user's feet. For example, populate the electronic notification with a "Yes" input field and a "No" input field; the user can thus confirm presence of inflammation by selecting the "Yes" input field and refute presence of inflammation by selecting the "No" input field directly through the electronic notification. In another example, the application can populate the electronic communication with photographic images of healthy feet and feet with varying degrees of inflammation; the user can thus select a photographic image—from this set—most representative of the current state of both feet or the current state of the foot predicted to be inflamed. In yet another example, the application can insert a slider bar into the electronic notification; to provide feedback, the user can adjust a slider on the slider bar between a "no inflammation" end and a "highly inflamed" opposite end of the slider bar.

The application can then adjust the threshold difference or other inflammation prediction module based on the user's feedback (or feedback from the other entity). For example, the application can: predict inflammation in the user's left foot following detection of a high temperature in the user's left foot and a temperature difference that exceeds the baseline temperature difference by more than an initial threshold difference; serve an electronic notification to inspect the user's left foot to the user through the computing device responsive to this inflammation prediction; receive affirmation of absence of inflammation in the user's left foot responsive to the electronic notification; and then increase the threshold difference (e.g., by 0.3° C.) in response to such affirmation of absence of inflammation in the user's left foot. In particular, if the user indicates through the user interface that no inflammation is visually or tactilely perceptible to the user, the application can interpret this feedback as viability of a greater temperature difference between the corresponding regions of the user's healthy left and right feet and then increase the threshold difference accordingly. (Similarly, in response to such affirmation that no inflammation is present, the application can adjust an inflammation prediction module to output a lower probability of inflammation at the temperature difference between like regions of the user's left and right feet that initially triggered this electronic notification.) However, if the user indicates through the user interface that inflammation is visually or tactilely perceptible, the application can interpret this feedback as possible late prediction of inflammation in the user's feet and decrease the threshold difference accordingly (e.g., by 0.2° C.). (Similarly, in response to such affirmation that inflammation is present, the application can adjust an inflammation prediction module to output a higher probability of inflammation at the temperature difference between like regions of the user's left and right feet that initially triggered this electronic notification.) Furthermore, in the examples described above in which the user provides feedback indicative of the extent of inflammation in the user's foot, the application can adjust the threshold difference proportional to the extent of inflammation indicated by the user.

7.2 Graphical User Interface

As shown in FIGS. 1-3, the application can present foot temperature data, foot condition diagnoses, sock function data, and related information to the user through a user interface executing within the application. For example, the application can display virtual representations of a left foot and a right foot overlaid with regions colored according to the absolute or relative temperature read from temperature sensors in corresponding positions within the left and right socks. In this example, the application: can render green circles over each region of the virtual left foot and right foot corresponding to temperature sensors from which temperatures fall within a first temperature range associated with a healthy condition; and can render red circles or other indicators over each region of the virtual left foot and right foot corresponding to temperature sensors from which temperatures fall within a second temperature range associated with inflammation (or other medical condition) exceeding a threshold probability. In Block S130, the application can prompt the user to manually inspect regions of her feet corresponding to red overlay circles on the virtual left and right feet rendered in the graphical user interface.

Alternatively, the application can assign a color to each circular area overlaid on the virtual left foot and right foot based on a relative or absolute temperature read from each temperature sensor, such as on a color scale from "blue" (representing a low temperature) to "red" (representing a high temperature). In this example, the application can prompt the user: to manually inspect regions of her feet corresponding to red overlay circles on the virtual left foot and right foot shown in the graphical user interface for sores; and to manually inspect regions of her feet corresponding to blue overlay circles on the virtual left foot and right foot shown in the graphical user interface for poor blood circulation.

As described above, the application can prompt the user to provide feedback regarding whether inflammation (or a sore or other physical condition)—suggested by a high temperature difference between two like regions on the user's left and right feet—is visible on one of the user's feet. For example, the application can prompt the user: to select one of the circular overlays in order to access a submenu for this region of the user's foot; and to then select a stock image—from a set of stock images—best visually representative of this region of the user's foot. In this example, the set of stock images can include a set of digital photographs or renderings exhibiting skin conditions ranging from healthy skin to gangrenous tissue, and each stock image can be labeled with a health of the skin shown or a severity of tissue condition represented. The user can thus select a stock image best representative of the user's skin at various regions represented in the virtual left foot and right foot, and the application can confirm or refute the predicted inflammation in the user's foot based on this selection. As described above, the application can also customize a threshold difference, template image labels, and/or an inflammation model for the user based on this feedback supplied by the user.

In a similar example, the application: can serve textual descriptions of visual symptoms of a skin or tissue condition in a submenu corresponding to a region of the virtual left and right feet; can prompt the user to select textual descriptions of symptoms that describe the visual state of this region of the user's foot; and can respond to this feedback confirming the inflammation prediction, such as by updating an inflammation model for the user or by escalating a notification to a doctor, nurse, emergency personnel, or other care provider to respond to a confirmed inflammation.

The application can additionally or alternatively render a virtual graph showing absolute or relative temperatures of various regions of the user's feet or an average temperature of each of the user's feet over time. For example, the application can serve temperature data to the user through a virtual graph in order to visually communicate to the user a trend in temperatures of or temperature differences between the user's feet over hours, days, weeks, or months, which may indicate a change in the health of the user's feet. In this example, the application can update the graph in real-time as data is received from sensors in the left and right socks.

However, the application can serve temperature data, medical diagnoses, and/or prompts for user feedback to the user in any other way through the graphical user interface at the user's mobile computing device.

7.3 Physical Activity Reduction

In another implementation shown in FIG. 5, in response to calculation of a binary prediction of inflammation in one of the user's feet (e.g., in response to a temperature difference that exceeds the baseline temperature difference by more than the threshold difference) and/or calculation of a probability of inflammation in the user's feet that exceeds a preset threshold probability (e.g., 65%), the application generates a prompt to reduce activity level and serves this prompt to the user, such as through a push notification rendered on the display of the computing device. In particular, if inflammation is developing in a foot, reduction in physical activity may reduce impact and stress on the affected region of the foot and thus lead to reduction in local inflammation. Therefore, if inflammation is detected or predicted in one of the user's feet, the application can generate an electronic notification containing a prompt to reduce physical activity for a subsequent duration of time, such as one hour, four hours, or a full day. In this example, the application can populate the electronic notification with a textual prompt suggesting the user reduce her physical activity, transition from jogging to walking, transition from standing to sitting, or transition from sitting to laying in a prone position.

In this implementation, the application can track the user's activity level, as described above, both before and after prompting the user to reduce her activity level. For example, the application can: estimate the user's activity level throughout a monitoring period based on motion data recorded through a motion sensor integrated into either sock or integrated into the computing device; later serve a prompt to the user to reduce her activity level over a duration of time (e.g., four hours) following detection or prediction of developing inflammation in one of the user's feet; and then confirm reduction in the user's physical activity throughout the duration of time based on a difference in activity levels of the user before and after serving this prompt. Throughout this duration of suggested reduction in activity level, the application can also implement methods and techniques described above to continue to monitor temperatures in the user's feet for signs of persistent, increased, or decreased inflammation. Subsequently, if the application detects a reduction in the user's physical activity concurrent with a persistent (e.g., unchanged or increasing) temperature difference between like regions of the user's feet (e.g., that exceeds the baseline temperature difference by more than the threshold difference), the application can determine that the user may require additional personal care or professional assistance. For example, the application can generate a second electronic notification containing a prompt to monitor the user and then transmit this second electronic notification to an electronic account associated with a care provider (e.g., a nurse, doctor, or family member) affiliated with the user.

Similarly, if the application determines or predicts a decrease in inflammation in the user's feet concurrent with a reduction in physical activity following delivery of the prompt to the user, the application can associate reduction in physical activity by the user with reduction in inflammation in the user's feet based on this data. The application can refine or customize a model or decision tree for handling detected or predicted inflammation in the user's feet accordingly. In this implementation, the application can also prompt the user (or an affiliated care provider or other entity) to provide feedback relating the presence and/or severity of inflammation in a region of the user's feet before, during, and/or after a prescribed period of reduced physical activity. As described above, the application can similarly adjust a model or decision tree for handling detected or predicted inflammation in the user's feet based on such feedback.

The application can also inform the user—through the user interface—of an absolute or relative degree to which a change in the user's physical activity has improved (or worsened) inflammation in the user's feet (e.g., a temperature difference between like regions of the user's feet).

Furthermore, if the application determines that the user's physical activity has not sufficiently decreased following delivery of such a prompt, the application can: serve the prompt to the user a second time; and/or serve a second prompt to assist the user in decreasing her activity level to a care provider.

8. Remote Monitoring

In one variation, the application can push temperature data and/or inflammation predictions to a remote care provider, such as to a computing device or care provider portal associated with a nurse, doctor, or emergency responder. A care provider can thus view temperature data and/or inflammation predictions for the user's feet in (near) real-time through the care provider portal and respond accordingly, such as by: visiting the user (e.g., for the care provider and user occupying an assisted living facility, hospital, or clinic); calling the user via telephone; scheduling an appointment with the user at a doctor's office; or dispatching an emergency responder to collect the user from the user's current location. Following the care provider's observation of the user, the care provider portal can implement methods and techniques as described above to collect feedback relating to the state of the user's feet from the care provider.

The application can also write temperature data, inflammation predictions, inflammation probabilities, and/or user feedback directly to an electronic health record associated with the user and stored in a local or remote database.

9. Compliance

In one variation, the application can also cooperate with socks in the kit to monitor the user's compliance with a directive to wear socks in the kit (e.g., to enable automatic or remote monitoring of inflammation in her feet). For example, the application can access a temperature monitoring schedule for the user, such as defined by the user's doctor and stored in a local or remote database. In this example, the temperature monitoring schedule can define one or more temperature monitoring periods, such as 8 AM to 6 PM on weekdays and 10 AM to 8 PM on weekends. During operation, upon determining its placement on a foot, the left sock can transmit confirmation that it is in place on a foot to the computing device executing the application; and upon determining its placement on a foot, the right sock can transmit confirmation that it is in place on a foot to the computing device executing the application, as described above. In particular, during operation, the application can intermittently (and regularly) receive confirmation of placement on a user's foot from one left sock and one right sock in the kit. The application can compare such confirmation—and absence of confirmation—to the predefined temperature monitoring periods to determine whether the user is complying with the temperature monitoring schedule. In particular, in response to absence of confirmation that a sock, in a set of socks associated with the user, is in place on a foot during a predefined temperature monitoring period, the application can determine that the user is not complying with the temperature monitoring schedule. The application can thus generate an electronic notification containing a prompt to place a pair of socks, in the kit, on her feet and then serve this electronic notification to the user, such as through the user interface executing on the user's mobile computing device. The application can also notify a care provider or other affiliate of the user's compliance or non-compliance with the temperature monitoring schedule.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a controller but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A system for monitoring a user, the system comprising:
   a garment configured to be placed on a foot of the user, the garment comprising
      one or more temperature sensors to measure at least one temperature on a sole of the foot of the user; and
   a computing device comprising a processor configured to:
      receive, at a first sampling rate, first temperature data from the one or more temperature sensors during a first time period;
      calculate a baseline temperature of the foot of the user based on the first temperature data;
      receive, at a second sampling rate, second temperature data from the one or more temperature sensors during a second time period, the second sampling rate being greater than the first sampling rate;
      determine at least one sampled temperature difference based on the second temperature data, wherein the at least one sampled temperature difference is determined as a difference between a temperature at a target region on the sole of the foot during the first time period and a temperature at the target region on the sole of the foot during the second time period;
      predict inflammation in at least the target region based on the at least one sampled temperature difference exceeding a predetermined threshold difference; and
      trigger an alarm in response to the predicted inflammation.

2. The system of claim 1, wherein the garment further comprises one or more sensors configured to indicate placement of the garment on the foot of the user.

3. The system of claim 2, wherein the one or more sensors comprise at least one of an accelerometer and a gyroscope.

4. The system of claim 2, wherein the processor is further configured to
   determine the placement of the garment on the foot of the user, and
   receive the first temperature data after positively determining the placement of the garment on the foot of the user.

5. The system of claim 1, wherein the one or more temperature sensors comprise a plurality of temperature sensors arranged in multiple distinct regions of the sole of the foot.

6. The system of claim 5, wherein the plurality of temperature sensors comprise at least one temperature sensor arranged in an ossa digit region of the garment, at least one temperature sensor arranged between a phalange region and a metatarsal region of the garment, at least one temperature sensor arranged between the metatarsal region and a tarsal region of the garment, and at least one temperature sensor arranged in a heel region of the garment.

7. The system of claim 1, wherein the garment further comprises an anklet housing a power supply and a memory.

8. A system for monitoring a user, the system comprising:
   a garment configured to be placed on a foot of the user, the garment comprising
      a plurality of temperature sensors arranged in multiple distinct regions of a sole of the foot of the user to measure a plurality of temperatures on the sole of the foot of the user;

and
a computing device comprising a processor configured to:
receive, at a first sampling rate, first temperature data from the plurality of temperature sensors during a first time period;
calculate, as a baseline temperature, a linear combination of the first temperature data from the plurality of temperature sensors;
receive, at a second sampling rate, second temperature data from the plurality of temperature sensors during a second time period, wherein the second sampling rate is greater than the first sampling rate;
determine a plurality of sampled temperature differences for each of the plurality of temperature sensors based on the second temperature data, wherein each sampled temperature difference is determined as a temperature difference between a region on the sole of the foot and the baseline temperature;
predict inflammation in at least one of the multiple distinct regions of the sole of the foot based on a comparison of the plurality of sampled temperature differences and a predetermined threshold difference; and
trigger an alarm through an interface of the computing device when inflammation is predicted.

9. The system of claim 8, wherein the garment further comprises one or more sensors configured to measure a state of the user and the processor is further configured to
determine the user state based on data from the one or more sensors; and
receive the second temperature data when the user state is determined to be in motion.

10. The system of claim 8, wherein the garment further comprises one or more sensors configured to indicate placement of the garment on the foot of the user.

11. The system of claim 9, wherein the processor is further configured to
determine placement of the garment on the foot of the user, and
receive the first temperature data after positively determining the placement of the garment on the foot of the user.

12. The system of claim 8, wherein the plurality of temperature sensors arranged within the multiple distinct regions of the sole of the foot comprise at least one temperature sensor arranged in an ossa digit region of the garment, at least one temperature sensor arranged between a phalange region and a metatarsal region of the garment, at least one temperature sensor arranged between the metatarsal region and a tarsal region of the garment, and at least one temperature sensor arranged in a heel region of the garment.

13. The system of claim 8, wherein the garment further comprises an anklet housing a power supply and a memory.

14. A system for monitoring a user, the system comprising:
a garment configured to be placed on a foot of the user, the garment comprising
one or more temperature sensors to measure at least one temperature on a sole of the foot of the user; and
a computing device comprising a processor configured to:
receive first temperature data from the one or more temperature sensors during a first time period;
receive second temperature data from the one or more temperature sensors during a second time period;
calculate a trend line based on the first temperature data and the second temperature data;
based on a magnitude and a direction of a slope of the trend line, predict inflammation in the foot of the user; and
trigger an alarm in response to the predicted inflammation.

15. The system of claim 14, wherein the garment further comprises one or more sensors configured to indicate placement of the garment on the foot of the user.

16. The system of claim 15, wherein the one or more sensors comprise at least one of an accelerometer and a gyroscope.

17. The system of claim 15, wherein the processor is further configured to
determine the placement of the garment on the foot of the user, and
receive the first temperature data from the one or more temperature sensors after positively determining the placement of the garment on the foot of the user.

18. The system of claim 14, wherein the one or more temperature sensors comprise a plurality of temperature sensors arranged in multiple distinct regions of the sole of the foot.

19. The system of claim 18, wherein the plurality of temperature sensors comprise at least one temperature sensor arranged in an ossa digit region of the garment, at least one temperature sensor arranged between a phalange region and a metatarsal region of the garment, at least one temperature sensor arranged between the metatarsal region and a tarsal region of the garment, and at least one temperature sensor arranged in a heel region of the garment.

20. The system of claim 14, wherein the garment further comprises an anklet housing a power supply and a memory.

* * * * *